United States Patent
Palmer et al.

(10) Patent No.: US 9,855,036 B2
(45) Date of Patent: Jan. 2, 2018

(54) STAPLES FOR GENERATING AND APPLYING COMPRESSION WITHIN A BODY

(71) Applicant: Arthrex, Inc., Naples, FL (US)

(72) Inventors: Matthew Palmer, Cambridge, MA (US); Matthew Fonte, Concord, MA (US); Robert Devaney, Auburndale, MA (US)

(73) Assignee: Arthrex, Inc., Naples, FL (US)

( * ) Notice: Subject to any disclaimer, the term of this patent is extended or adjusted under 35 U.S.C. 154(b) by 425 days.

(21) Appl. No.: 14/540,351

(22) Filed: Nov. 13, 2014

(65) Prior Publication Data

US 2015/0133940 A1    May 14, 2015

Related U.S. Application Data

(60) Provisional application No. 61/903,820, filed on Nov. 13, 2013.

(51) Int. Cl.
*A61B 17/06* (2006.01)
*A61B 17/064* (2006.01)
(Continued)

(52) U.S. Cl.
CPC ...... *A61B 17/0642* (2013.01); *A61B 17/0682* (2013.01); *A61B 17/7266* (2013.01);
(Continued)

(58) Field of Classification Search
CPC .................................................. A61B 17/0642
See application file for complete search history.

(56) References Cited

U.S. PATENT DOCUMENTS

| 2,580,821 A | 1/1952 | Nicola |
| 3,960,147 A | 6/1976 | Murray |

(Continued)

FOREIGN PATENT DOCUMENTS

| EP | 0826340 A2 | 3/2008 |
| FR | 2787313 A1 | 6/2000 |

(Continued)

OTHER PUBLICATIONS

Huang et al., Ion release from NiTi orthodontic wires in artificial saliva with various acidities, Biomaterials, 24, 2003, 3585-3592.
(Continued)

*Primary Examiner* — Andrew Yang
(74) *Attorney, Agent, or Firm* — Carlson, Gaskey & Olds, P.C.

(57) ABSTRACT

A staple comprising: a bridge configured to be elastically stretchable; a first leg connected to said bridge and configured to be elastically bendable; and a second leg connected to said bridge and configured to be elastically bendable; said first and second legs being connected to said bridge so that they are angled toward one another when they are in an unstrained state; such that when said bridge is elastically strained into an elongated condition, and said first and second legs are elastically strained so that they extend substantially parallel to one another, and said first and second legs are disposed in appropriate holes on opposing sides of a fracture line, and when the strain on said staple is thereafter released, compression will be provided across the fracture line by both said bridge and said first and second legs.

17 Claims, 25 Drawing Sheets

(51) Int. Cl.
  *A61B 17/068* (2006.01)
  *A61B 17/72* (2006.01)
  *A61B 17/00* (2006.01)

(52) U.S. Cl.
  CPC .............. *A61B 17/7291* (2013.01); *A61B 2017/00867* (2013.01); *A61B 2017/00871* (2013.01); *A61B 2017/00946* (2013.01); *A61B 2017/0645* (2013.01)

(56) References Cited

U.S. PATENT DOCUMENTS

| | | |
|---|---|---|
| 4,175,555 A | 11/1979 | Herbert |
| 4,428,376 A | 1/1984 | Mericle |
| 4,444,181 A | 4/1984 | Wevers et al. |
| 4,503,569 A | 3/1985 | Dotter |
| 4,512,338 A | 4/1985 | Balko et al. |
| 4,570,623 A | 2/1986 | Ellison et al. |
| 4,733,665 A | 3/1988 | Palmaz |
| 4,858,601 A | 8/1989 | Glisson |
| 4,905,679 A | 3/1990 | Morgan |
| 4,922,905 A | 5/1990 | Strecker |
| 4,950,227 A | 8/1990 | Savin et al. |
| 4,959,064 A | 9/1990 | Engelhardt |
| 4,959,065 A | 9/1990 | Arnett et al. |
| 5,026,390 A | 6/1991 | Brown |
| 5,044,540 A | 9/1991 | Dulebohn |
| 5,061,275 A | 10/1991 | Wallsten et al. |
| 5,089,006 A | 2/1992 | Stiles |
| 5,098,434 A | 3/1992 | Serbousek |
| 5,246,443 A | 9/1993 | Mai |
| 5,474,557 A | 12/1995 | Mai |
| 5,607,530 A | 3/1997 | Hall et al. |
| 5,680,981 A | 10/1997 | Mililli et al. |
| 5,766,218 A | 6/1998 | Arnott |
| 5,779,707 A | 7/1998 | Bertholet et al. |
| 5,876,434 A | 3/1999 | Flomenblit et al. |
| 5,947,999 A | 9/1999 | Groiso |
| 6,030,162 A | 2/2000 | Huebner |
| 6,048,344 A | 4/2000 | Schenk |
| 6,187,009 B1 | 2/2001 | Herzog et al. |
| 6,306,140 B1 | 10/2001 | Siddiqui |
| 6,325,805 B1 | 12/2001 | Ogilvie et al. |
| 6,533,157 B1 | 3/2003 | Whitman |
| 6,569,173 B1 | 5/2003 | Blatter et al. |
| 6,607,530 B1 | 8/2003 | Carl et al. |
| 6,623,486 B1 | 9/2003 | Weaver et al. |
| 6,656,184 B1 | 12/2003 | White et al. |
| 6,685,708 B2 | 2/2004 | Monassevitch et al. |
| 6,761,731 B2 | 7/2004 | Majercak |
| 6,773,437 B2 | 8/2004 | Ogilvie et al. |
| 7,175,626 B2 | 2/2007 | Neff |
| 7,229,452 B2 | 6/2007 | Kayan |
| 7,481,832 B1 | 1/2009 | Meridew et al. |
| 7,582,107 B2 | 9/2009 | Trail et al. |
| 7,618,441 B2 | 11/2009 | Groiso |
| 7,625,395 B2 | 12/2009 | Muckter |
| 7,794,483 B2 | 9/2010 | Capanni |
| 7,875,070 B2 | 1/2011 | Molaei |
| 7,955,388 B2 | 6/2011 | Jensen et al. |
| 7,976,648 B1 | 7/2011 | Boylan et al. |
| 7,985,222 B2 | 7/2011 | Gall et al. |
| 7,993,380 B2 | 8/2011 | Hawkes |
| 8,048,134 B2 | 11/2011 | Partin |
| 8,080,044 B2 | 12/2011 | Biedermann et al. |
| 8,114,141 B2 | 2/2012 | Appenzeller et al. |
| 8,118,952 B2 | 2/2012 | Gall et al. |
| 8,137,351 B2 | 3/2012 | Prandi |
| 8,216,398 B2 | 7/2012 | Bledsoe et al. |
| 8,221,478 B2 | 7/2012 | Patterson et al. |
| 8,393,517 B2 | 3/2013 | Milo |
| 8,425,588 B2 | 4/2013 | Molaei |
| 8,486,121 B2 | 7/2013 | Biedermann et al. |
| 8,584,853 B2 | 11/2013 | Knight et al. |
| 8,597,337 B2 | 12/2013 | Champagne |
| 8,721,646 B2 | 5/2014 | Fox |
| 8,790,379 B2 | 7/2014 | Bottlang et al. |
| 8,801,732 B2 | 8/2014 | Harris et al. |
| 8,808,294 B2 | 8/2014 | Fox et al. |
| 8,864,804 B2 | 10/2014 | Champagne et al. |
| 9,017,331 B2 | 4/2015 | Fox |
| 9,095,338 B2 | 8/2015 | Taylor et al. |
| 9,101,349 B2 | 8/2015 | Knight et al. |
| 9,204,932 B2 | 12/2015 | Knight et al. |
| 9,326,804 B2 | 5/2016 | Biedermann et al. |
| 9,339,268 B2 | 5/2016 | Fox |
| 9,408,647 B2 | 8/2016 | Cheney |
| 9,451,955 B2 | 9/2016 | Fox |
| 9,451,957 B2 | 9/2016 | Fox |
| 2002/0058940 A1 | 5/2002 | Frigg et al. |
| 2002/0111641 A1 | 8/2002 | Peterson et al. |
| 2002/0198527 A1 | 12/2002 | Muckter |
| 2004/0111089 A1 | 6/2004 | Stevens et al. |
| 2004/0230193 A1 | 11/2004 | Cheung et al. |
| 2004/0260377 A1 | 12/2004 | Flomenblit et al. |
| 2005/0043757 A1 | 2/2005 | Arad et al. |
| 2005/0096660 A1 | 5/2005 | Allen |
| 2005/0152770 A1 | 7/2005 | Tschakaloff et al. |
| 2005/0277940 A1 | 12/2005 | Neff |
| 2005/0288707 A1 | 12/2005 | De Canniere et al. |
| 2006/0264954 A1 | 11/2006 | Sweeney, II et al. |
| 2007/0233124 A1 | 10/2007 | Corrao et al. |
| 2007/0260248 A1 | 11/2007 | Tipirneni |
| 2007/0265631 A1 | 11/2007 | Fox |
| 2007/0270855 A1 | 11/2007 | Partin |
| 2008/0065154 A1 | 3/2008 | Allard et al. |
| 2008/0071373 A1 | 3/2008 | Molz et al. |
| 2008/0132894 A1 | 6/2008 | Coilard-Lavirotte et al. |
| 2008/0234763 A1 | 9/2008 | Patterson et al. |
| 2008/0249574 A1 | 10/2008 | McCombs et al. |
| 2009/0018556 A1 | 1/2009 | Prandi |
| 2009/0105768 A1 | 4/2009 | Cragg et al. |
| 2009/0198287 A1 | 8/2009 | Chiu |
| 2009/0254090 A1 | 10/2009 | Lizee |
| 2009/0264937 A1 | 10/2009 | Parrott |
| 2010/0036430 A1 | 2/2010 | Hartdegen et al. |
| 2010/0063506 A1 | 3/2010 | Fox et al. |
| 2010/0087822 A1 | 4/2010 | Groiso |
| 2010/0131014 A1 | 5/2010 | Peyrot et al. |
| 2010/0211115 A1 | 8/2010 | Tyber et al. |
| 2010/0237128 A1 | 9/2010 | Miller et al. |
| 2011/0008643 A1 | 1/2011 | Shaw et al. |
| 2011/0060372 A1 | 3/2011 | Allison |
| 2011/0144703 A1 | 6/2011 | Krause et al. |
| 2011/0224725 A1 | 9/2011 | De Canniere et al. |
| 2011/0247731 A1 | 10/2011 | Gordon |
| 2011/0313473 A1 | 12/2011 | Prandi et al. |
| 2012/0116465 A1 | 5/2012 | Elahinia et al. |
| 2013/0030437 A1 | 1/2013 | Fox |
| 2013/0066435 A1 | 3/2013 | Averous et al. |
| 2013/0123785 A1 | 5/2013 | Fonte |
| 2013/0206815 A1 | 8/2013 | Fox |
| 2013/0231667 A1 | 9/2013 | Taylor et al. |
| 2013/0300437 A1 | 11/2013 | Grosjean et al. |
| 2014/0014553 A1 | 1/2014 | Knight et al. |
| 2014/0018809 A1 | 1/2014 | Allen |
| 2014/0020333 A1 | 1/2014 | Knight et al. |
| 2014/0024002 A1 | 1/2014 | Knight et al. |
| 2014/0097228 A1 | 4/2014 | Taylor et al. |
| 2014/0257420 A1 | 9/2014 | Fox |
| 2014/0277516 A1 | 9/2014 | Miller et al. |
| 2014/0324048 A1 | 10/2014 | Fox |
| 2014/0358187 A1 | 12/2014 | Taber et al. |
| 2014/0358247 A1 | 12/2014 | Fox et al. |
| 2015/0238237 A1 | 8/2015 | Madjarov |
| 2015/0238238 A1 | 8/2015 | Cheney |
| 2016/0051284 A1 | 2/2016 | Cronen |
| 2016/0089190 A1 | 3/2016 | Taber |
| 2016/0095638 A1 | 4/2016 | Reimels |
| 2016/0135808 A1 | 5/2016 | Anderson |
| 2016/0199060 A1 | 7/2016 | Morgan et al. |
| 2016/0235460 A1 | 8/2016 | Wahl |

(56) References Cited

U.S. PATENT DOCUMENTS

2017/0000482 A1 1/2017 Averous et al.
2017/0231625 A1 8/2017 Handie

FOREIGN PATENT DOCUMENTS

| FR | 2874166 A1 | 2/2006 |
|---|---|---|
| FR | 2901119 A1 | 11/2007 |
| IL | 64726 A | 2/1985 |
| WO | 2009/091770 A1 | 7/2009 |
| WO | 2014087111 A1 | 6/2014 |

OTHER PUBLICATIONS

Gruszka et al., The Durability of the Intrascaphoid Compression of Heatless Compression Screws: In Vitro Study, JHS, vol. 37A, Jun. 2012, 1142-1150.
S. Cai et al., Texture evolution during nitinol martensite detwinning and phase transformation, Appl. Phys. Lett. 103, 2013, 241909.
International Preliminary Report on Patentability for PCT Application No. PCT/US2014/065406 dated May 17, 2016.
International Preliminary Report on Patentability for PCT Application No. PCT/US2014/065553 dated May 17, 2016.
International Preliminary Report on Patentability for PCT Application No. PCT/US2015/020598 dated Sep. 13, 2016.
International Preliminary Report on Patentability for PCT Application No. PCT/US2015/028328 dated Nov. 1, 2016.
International Preliminary Report on Patentability for PCT Application No. PCT/US2016/015432 dated Aug. 10, 2017.
International Search Report and Written Opinion for PCT Application No. PCT/US2014/065406 dated Feb. 24, 2015.
International Search Report and Written Opinion for PCT Application No. PCT/US2014/065553 dated Feb. 24, 2015.
International Search Report and Written Opinion for PCT Application No. PCT/US2015/020598 dated Jun. 12, 2015.
International Search Report and Written Opinion for PCT Application No. PCT/US2015/028328 dated Aug. 4, 2015.
International Search Report and Written Opinion for PCT Application No. PCT/US2016/015432 dated Apr. 21, 2016.
International Search Report and Written Opinion for PCT Application No. PCT/US2016/023980 dated Jul. 21, 2106.
Non-Final Office Action for U.S. Appl. No. 15/539,650 dated Apr. 18, 2017.
U.S. Appl. No. 15/651,530 filed Jul. 17, 2017, entitled "Staples for Generating and Applying Compression within a Body".
Non-Final Office Action for U.S. Appl. No. 15/650,210 dated Oct. 4, 2017.
Non-Final Office Action for U.S. Appl. No. 15/684,183 dated Oct. 10, 2017.
Restriction Requirement for U.S. Appl. No. 14/699,837 dated Sep. 13, 2017.
Supplementary European Search Report for EP Application 14861059.5 dated Sep. 6, 2017.
Supplementary European Search Report for EP Application 14862438.0 dated Jun. 12, 2017.
Supplementary European Search Report for EP Application No. 14861238.5 dated Jun. 12, 2017.
U.S. Appl. No. 14/699,837 filed Apr. 29, 2015, entitled "Controlling the Unloading Stress of Nitinol Devices and/or Other Shape Memory Material Devices".
U.S. Appl. No. 15/079,770 filed Mar. 24, 2016, entitled "Staples for Generating and Applying Compression Within a Body".
U.S. Appl. No. 15/539,650 filed Nov. 12, 2014, entitled "Screws for Generating and Applying Compression Within a Body".
U.S. Appl. No. 15/684,183 filed Aug. 23, 2017, entitled "Staples for Generating and Applying Compression Within a Body".
U.S. Appl. No. 15/650,210 filed Jul. 14, 2017, entitled "Staples for Generating and Applying Compression Within a Body".

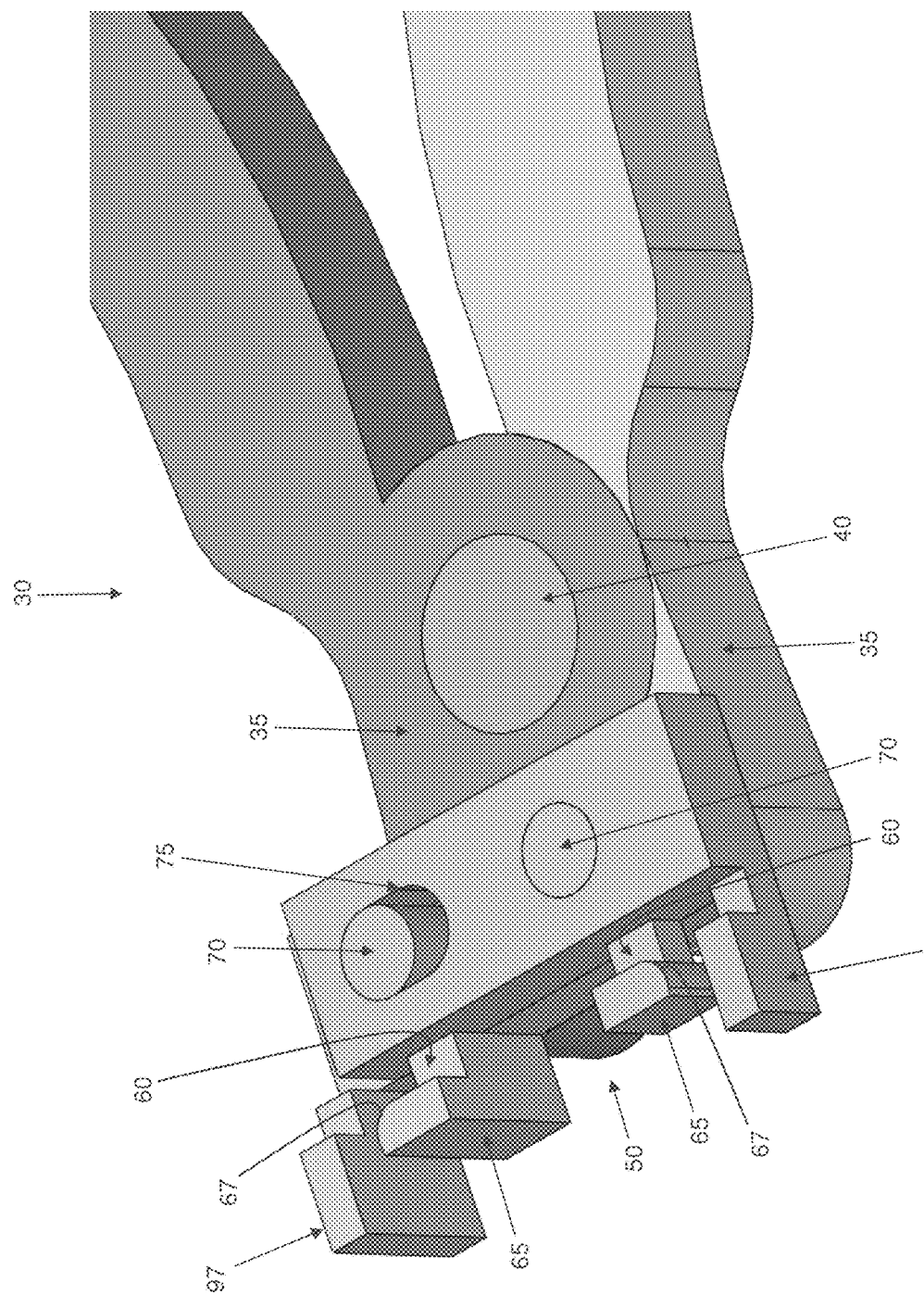

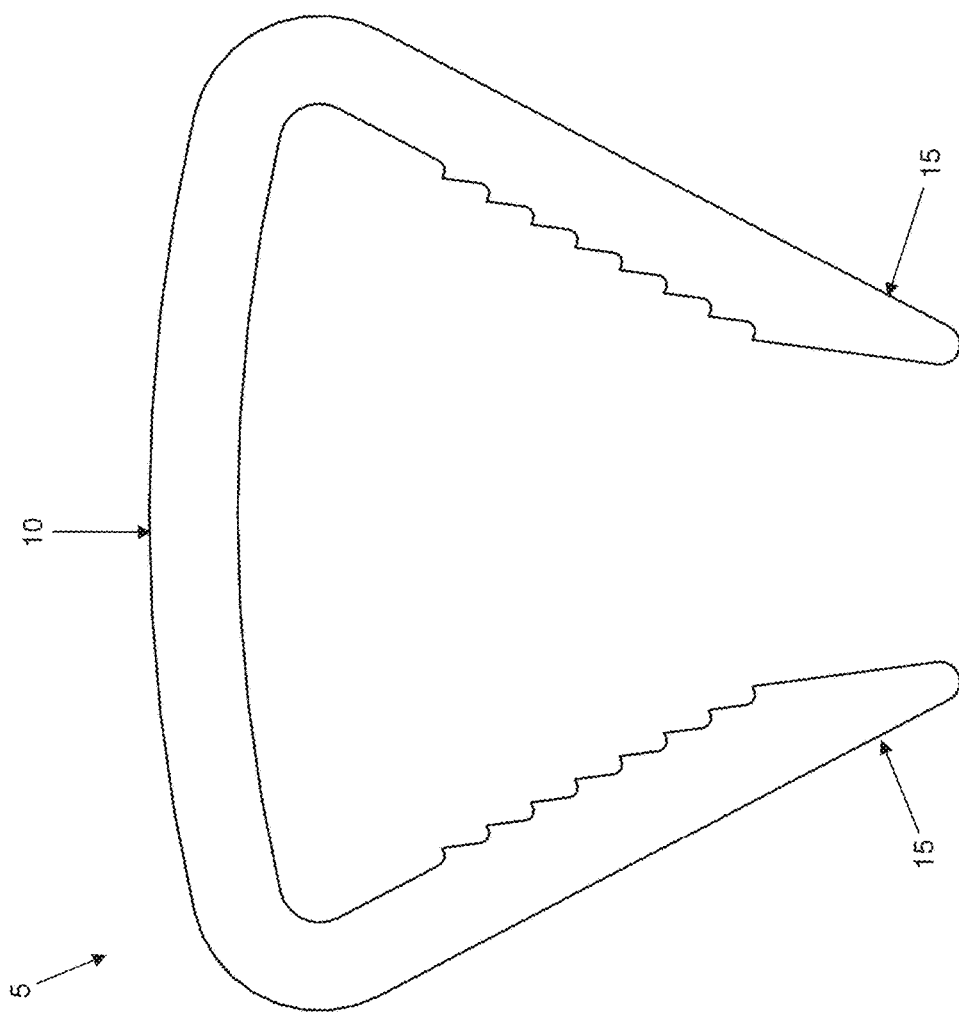

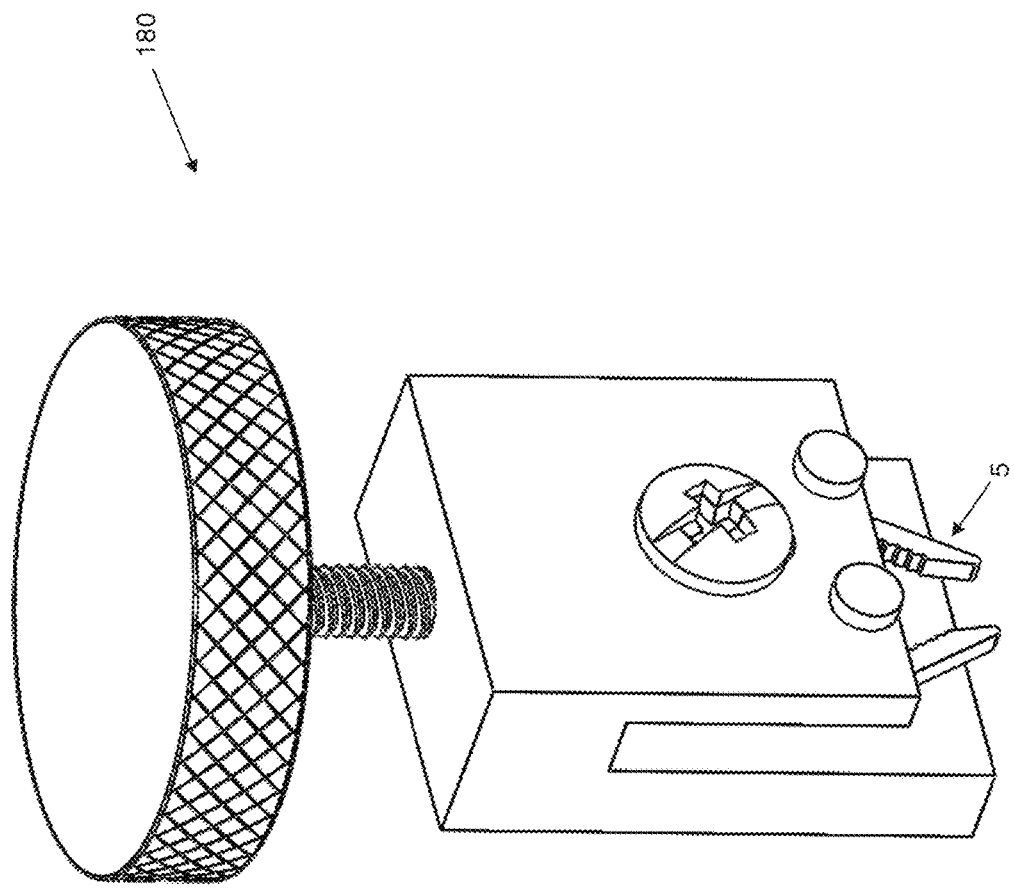

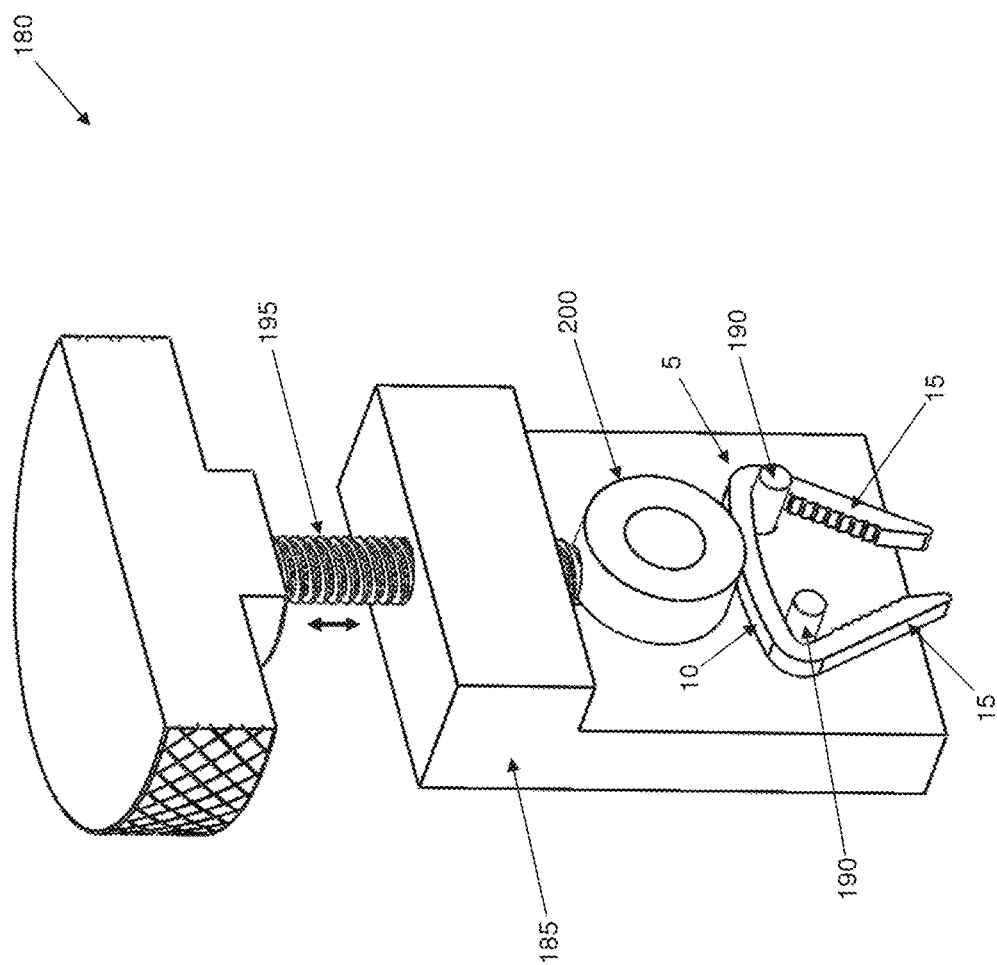

STAPLES FOR GENERATING AND APPLYING COMPRESSION WITHIN A BODY

REFERENCE TO PENDING PRIOR PATENT APPLICATION

This patent application claims benefit of prior U.S. Provisional Patent Application Ser. No. 61/903,820, filed Nov. 13, 2013 by MX Orthopedics, Corp. and Matthew Palmer et al. for BONE STAPLES, INTRAMEDULLARY FIXATION DEVICES, SOFT TISSUE ANCHORS AND PINS SCREWS CAN BE SHORTENED IN VIVO TO IMPROVE FRACTURE REDUCTION BY USING SUPERELASTIC OR SHAPE MEMORY EFFECT CHARACTERISTICS OF NITINOL, which patent application is hereby incorporated herein by reference.

FIELD OF THE INVENTION

The present invention relates to staples for generating, applying, and maintaining compression to a site in a human or animal body in order to facilitate healing of diseased or damaged tissue. The invention finds particular utility in the field of orthopedics and specifically for reducing fractures and maintaining compression between bone fragments. While the invention has application throughout the body, its utility will be illustrated herein in the context of the repair of fractured or displaced bone tissue, such as during an Akin Osteotomy of the foot or an Isolated Lunocapitate Arthrodesis of the hand/wrist.

BACKGROUND OF THE INVENTION

In the field of orthopedic surgery it is common to rejoin broken bones. The success of the surgical procedure often depends on the ability to reaproximate the fractured bones, the amount of compression achieved between the bone fragments, and the ability to sustain that compression over a period of time. If the surgeon is unable to bring the bone fragments into close contact, a gap will exist between the bone fragments and the bone tissue will need to fill that gap before complete healing can take place. Furthermore, gaps between bone fragments that are too large allow motion to occur between the bone fragments, disrupting the healing tissue and thus slowing the healing process. Optimal healing requires that the bone fragments be in close contact with each other, and for a compressive load to be applied and maintained between the bone fragments. Compressive strain between bone fragments has been found to accelerate the healing process in accordance with Wolf's Law.

Broken bones can be rejoined using staples. Staples are formed from a plurality of legs (typically two legs, though sometimes more) connected together by a bridge. Staples are typically manufactured from either stainless steel alloys, titanium alloys or Nitinol, a shape memory alloy. The staples are inserted into pre-drilled holes on either side of the fracture site.

While these staples are designed to bring the bone fragments into close contact and to generate a compressive load between the bone fragments, the staples do not always succeed in accomplishing this objective. It is widely reported that the compressive load of staples dissipates rapidly as the bone relaxes and remodels around the legs of the staples.

Thus there exists a clinical need for fixation devices that are able to bring bone fragments into close proximity with each other, generate a compressive load, and maintain that compressive load for a prolonged period of time while healing occurs.

Moreover, existing staples have bridges that are fixed in size, shape, and dimension, while each procedure presents a unique anatomical requirement (which is set by a combination of indication and patient-specific anatomy). Existing staples with fixed shape and dimension bridges will often sit "proud" of the cortical bone, resulting in irritated and inflamed adjacent soft tissue and, in some cases, bursitis.

Thus there also exists a clinical need for a staple with a malleable bridge that may be bent so as to conform to the unique anatomical structure of each patient and sit flush on the cortical surface of the bone.

SUMMARY OF THE INVENTION

The present invention provides a novel fixation device which is able to bring bone fragments into close proximity with each other, generate a compressive load, and maintain that compressive load for a prolonged period of time while healing occurs.

Among other things, the present invention comprises the provision and use of a novel monolithic staple which is manufactured from a single piece of shape memory material (e.g., a material capable of exhibiting superelasticity and/or a temperature-induced shape change). The shape memory material may be a metal alloy (e.g., Nitinol) or a polymer (e.g., appropriately processed PEEK). The staple is designed to reduce fractures and generate and maintain more uniform compression between the cortical bone and cancellous bone of the bone fragments to aid in fracture healing.

In one form of the invention, the staple comprises an elastic bridge and two elastic legs. The bridge and the legs meet at a pair of curved hinge regions which are also elastic. In the un-restrained state, the legs of the staple are bent inward with an angle of less than 90°. Prior to implantation, the bridge of the staple can be reversibly strained outward (i.e., stretched longitudinally outward) and the legs of the staple can be reversibly bent to a position perpendicular to the longitudinal axis of the bridge so as to allow for insertion of the staple into a prepared fracture site. A delivery device may be used to strain the bridge, bend the legs to parallel, hold the staple in this strained state prior to implantation, and insert the strained staple into the prepared fracture site. The constraint on the bridge and legs is removed, whereupon the bridge and legs attempt to return to their original unrestrained state, thereby generating a greater, and more uniform, compressive load and maintaining that greater, and more uniform, compressive load for a prolonged period of time while healing occurs.

In another form of the invention, the staple comprises a malleable bridge and two elastic legs. The bridge and the legs meet at a pair of curved hinge regions which are also elastic. In the unrestrained state, the legs of the staple are bent inward with an angle of less than 90°. Prior to implantation, the malleable bridge may be deformed so that it conforms to the unique anatomical structure of the patient, such that it will sit flush with the cortical surface of the bone after implantation. And prior to implantation, the legs of the staple can be reversibly bent to a position perpendicular to the longitudinal axis of the bridge so as to allow for insertion of the staple into a prepared fracture site. A bending device may be used to deform the bridge, and a delivery device may be used to hold the deformed bridge, bend the legs, hold the staple in this state prior to implantation, and insert the staple into the bone, with the bridge of the staple extending across the fracture line. Alternatively, a combined bending/delivery device may be used to deform the bridge, bend the legs, hold the staple in this condition prior to implantation, and insert the staple into the bone, with the bridge of the staple extending across the fracture line. Upon insertion of the deformed and strained staple into the prepared fracture site, the constraint on the legs of the staple is removed, whereupon the legs of the staple attempt to return to their original unrestrained state, thereby generating a compressive load and maintaining that compressive load for a prolonged period of time while healing occurs. Significantly, the deformed bridge of the staple can be matched to the unique anatomical structure of the patient, such that the bridge of the staple will sit flush with the cortical surface of the bone.

Additionally, it is possible that where the staple comprises a malleable bridge with two elastic legs, the staple can be inserted into the fracture site prior to bending the bridge. The bridge can be bent after implantation using a tamp-like device of the sort known in the art.

In one preferred form of the invention, there is provided a staple comprising:

a bridge configured to be elastically stretchable;
a first leg connected to said bridge and configured to be elastically bendable; and
a second leg connected to said bridge and configured to be elastically bendable;
said first and second legs being connected to said bridge so that they are angled toward one another when they are in an unstrained state;

such that when said bridge is elastically strained into an elongated condition, and said first and second legs are elastically strained so that they extend substantially parallel to one another, and said first and second legs are disposed in appropriate holes on opposing sides of a fracture line, and when the strain on said staple is thereafter released, compression will be provided across the fracture line by both said bridge and said first and second legs.

In another preferred form of the invention, there is provided a method for providing compression across a fracture line, the method comprising:

providing a staple comprising:
a bridge configured to be elastically stretchable;
a first leg connected to said bridge and configured to be elastically bendable; and
a second leg connected to said bridge and configured to be elastically bendable;
said first and second legs being connected to said bridge so that they are angled toward one another when they are in an unstrained state;
elastically straining said bridge into an elongated condition, and elastically straining said first and second legs so that they extend substantially parallel to one another;
inserting said first and second legs in appropriate holes on opposing sides of a fracture line; and
releasing the strain on said staple so that compression is provided across the fracture line by both said bridge and said first and second legs.

In another preferred form of the invention, there is provided a staple comprising:

a malleable bridge configured to be inelastically deformed;
a first leg connected to said bridge and configured to be elastically bendable; and
a second leg connected to said bridge and configured to be elastically bendable;
said first and second legs being connected to said bridge so that they are angled toward one another when they are in an unstrained state;

such that when said bridge is inelastically deformed, and said first and second legs are elastically strained so that they extend substantially parallel to one another, and said first and second legs are disposed in appropriate holes on opposing sides of a fracture line, and when the strain on said staple is thereafter released, compression will be provided across the fracture line by said first and second legs.

In another preferred form of the invention, there is provided a method for providing compression across a fracture line, the method comprising:

providing a staple comprising:
a malleable bridge configured to be inelastically deformed;
a first leg connected to said bridge and configured to be elastically bendable; and
a second leg connected to said bridge and configured to be elastically bendable;
said first and second legs being connected to said bridge so that they are angled toward one another when they are in an unstrained state;
inelastically deforming said bridge, and elastically straining said first and second legs so that they extend substantially parallel to one another;
inserting said first and second legs in appropriate holes on opposing sides of a fracture line; and
releasing the strain on said staple so that compression is provided across the fracture line by said first and second legs.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 8A, 8B and 8C are schematic views showing another form of delivery device which may be used with the novel staple shown in FIG. 1 to elastically strain (i.e., stretch) the bridge of the staple and elastically bend the legs of the staple;

FIGS. 9 and 10 are schematic views of another novel staple formed in accordance with the present invention, wherein the staple comprises a malleable bridge which is capable of being inelastically deformed and legs which are capable of being elastically strained, and further wherein FIG. 9 shows the staple in its unstrained condition and FIG. 10 shows the staple with its bridge bent but its legs in an unstrained condition;

FIG. 19 is a schematic view of another novel staple formed in accordance with the present invention, wherein the staple comprises a malleable bridge which is capable of being inelastically deformed and legs which are capable of being elastically strained, and further wherein the bridge of the staple has been deformed to have a convex configuration after bending; and FIGS. 20 and 21 are schematic views of another novel device which may be used to bend the bridge of the staple shown in FIG. 10A.

DETAILED DESCRIPTION OF THE PREFERRED EMBODIMENTS

Novel Staple Comprising Elastic Bridge with Two Elastic Legs

Figure 1:
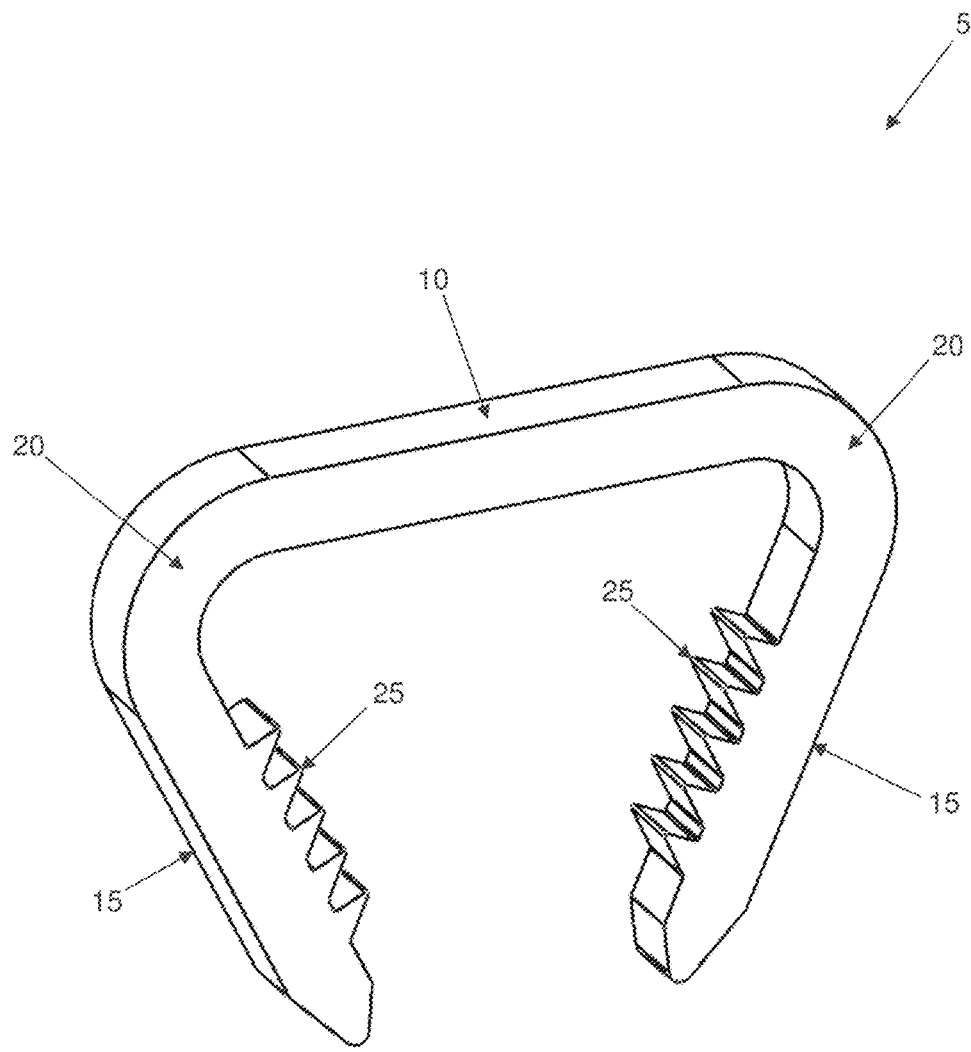
FIG. 1 is a schematic view of a novel staple formed in accordance with the present invention, wherein the staple comprises a bridge which is capable of being elastically strained and legs which are capable of being elastically strained, and further wherein the staple is shown in its unstrained condition.

Looking first at FIG. 1, there is shown a novel staple 5 which is able to bring bone fragments into close proximity with each other, generate a greater, and more uniform (i.e., across the cortical bone and the cancellous bone), compressive load across the fracture line, and maintain that greater, and more uniform, compressive load for a prolonged period of time while healing occurs.

Novel staple 5 is preferably an integral, monolithic structure manufactured from a single piece of shape memory material (e.g., a material capable of exhibiting superelasticity and/or a temperature-induced shape change). The shape memory material may be a metal alloy (e.g., Nitinol) or a polymer (e.g., appropriately processed PEEK). Staple 5 is designed to reduce fractures and generate and maintain greater, and more uniform, compression between bone fragments to aid in fracture healing. Staple 5 comprises an elastic bridge 10 and two elastic legs 15. Bridge 10 and legs 15 meet at a pair of curved hinge regions 20 which are also elastic. Legs 15 may have barbed teeth 25 to help the legs of the staple grip into the bone after implantation (see below) and prevent the legs of the staple from working their way back out of the bone. In the un-restrained state, legs 15 of staple 5 are bent inward with an angle of less than 90°. By way of example but not limitation, in one preferred form of the invention, legs 15 extend at an angle of about 45° to the longitudinal axis of bridge 10 when in their unrestrained state.

Figure 2:
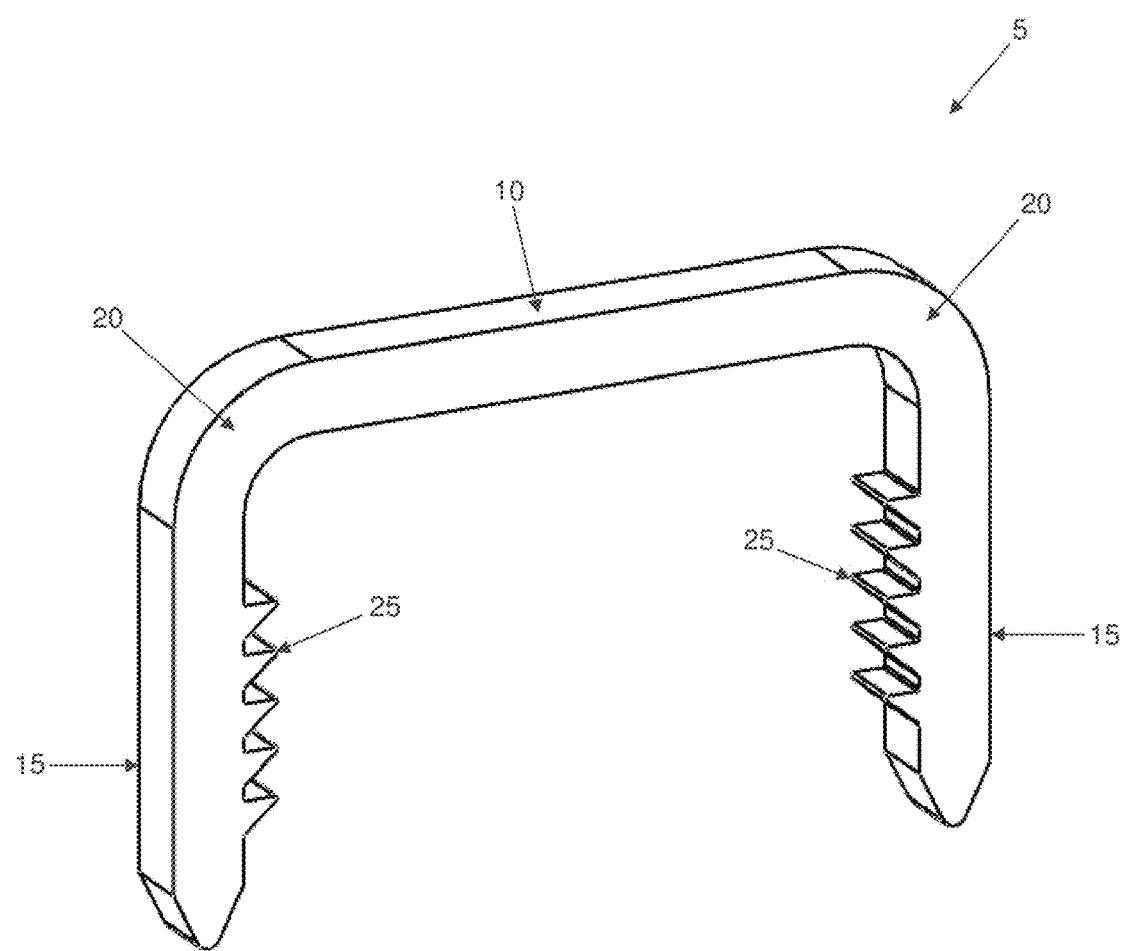
FIG. 2 is a schematic view of the novel staple shown in FIG. 1, wherein the bridge of the staple has been elastically strained (i.e., longitudinally stretched) and the legs of the staple have been elastically bent outwards.

Prior to implantation, bridge 10 of staple 5 can be reversibly strained outward (i.e., stretched longitudinally) and legs 15 of staple 5 can be reversibly bent to a position substantially perpendicular to bridge 10 (FIG. 2) so as to allow for insertion of the legs of the staple into a prepared fracture site, with the stretched bridge of the staple spanning across the fracture line (see below). Note that where staple 5 is formed out of Nitinol, elastic deformations of up to approximately 8% are achievable. A delivery device (see below) can be used to strain bridge 10 and to bend legs 15, hold the staple in this strained state prior to implantation, and then insert the staple into the prepared fracture site.

Figure 3:
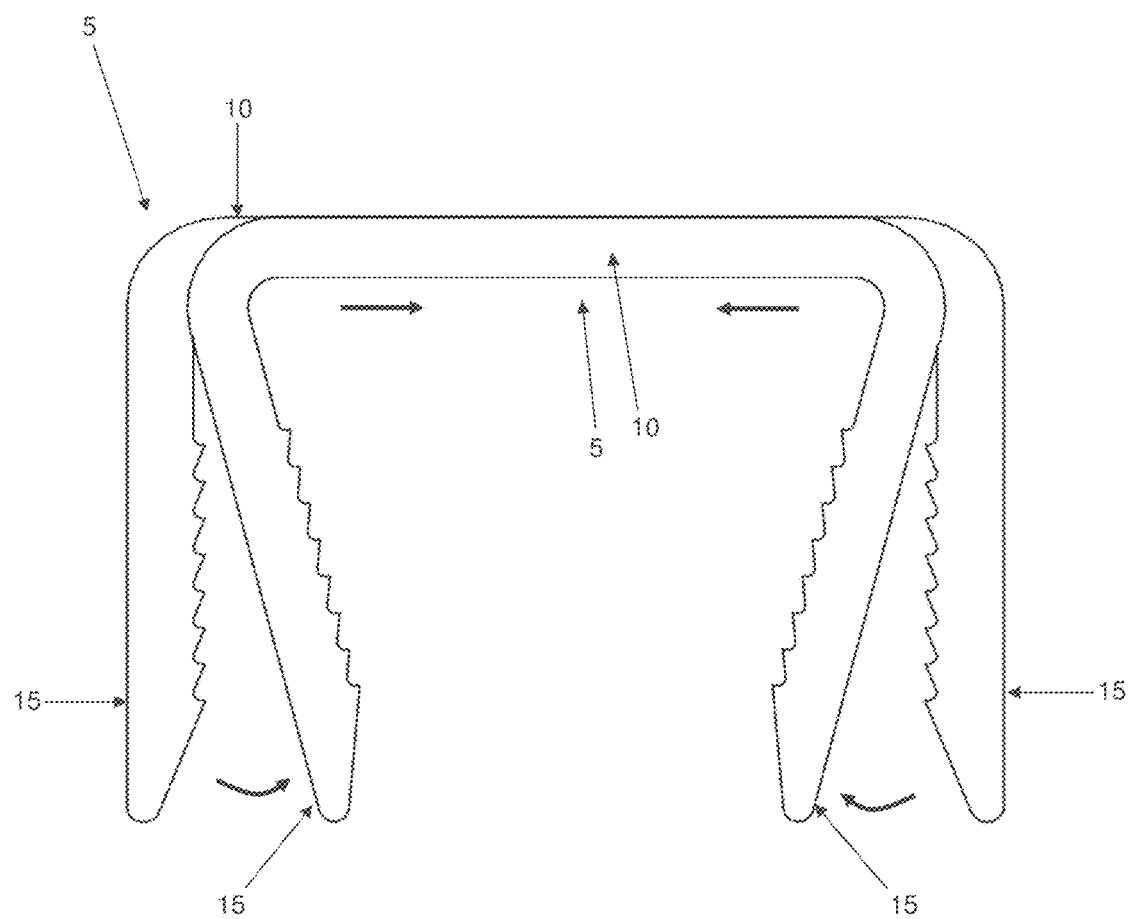
FIG. 3 is a schematic view showing how the elastically strained staple of FIG. 2 will foreshorten along its bridge, and have its legs "kick inward", when the strain on the staple is removed.
Figure 4:
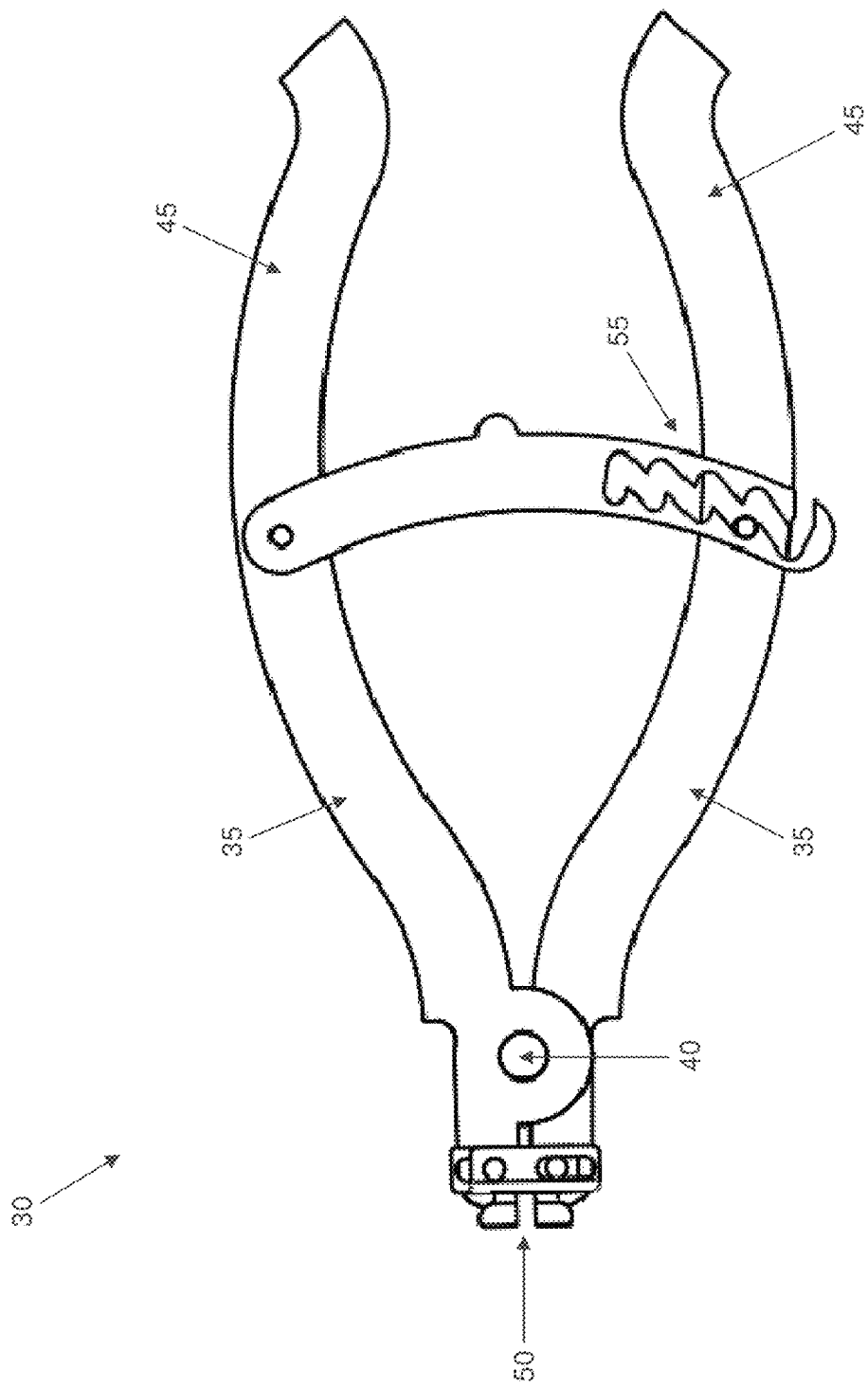
FIGS. 4 and 5 are schematic views showing an exemplary delivery device which may be used with the novel staple shown in FIG. 1 to elastically strain (i.e., stretch) the bridge of the staple and elastically bend the legs of the staple.

Upon insertion of the strained staple 5 into the prepared fracture site, the constraint on bridge 10 and legs 15 is removed, whereupon staple 5 attempts to return to its original un-restrained state (FIG. 3), thereby generating a greater compressive load with more uniformity along the fracture line (i.e., through legs 15 and compressive bridge 10), and maintaining that compressive load for a prolonged period of time while healing occurs.

Looking next at FIGS. 4-7, there is shown an exemplary delivery device 30 which may be used to strain (i.e., stretch) bridge 10 and bend legs 15 of staple 5. Delivery device 30 comprises two arms 35 which are pivotally connected together at a pivot pin 40, whereby to provide a pair of handles 45 on one end for actuating the delivery device, and a staple mount 50 on the other end for holding and straining staple 5. When staple 5 is mounted to staple mount 50 of delivery device 30 and handles 45 are thereafter moved toward one another, staple mount 50 translates apart, thus stretching bridge 10 of staple 5, and also bending legs 15 of staple 5 outward to a position substantially perpendicular to the longitudinal axis of bridge 10. Delivery device 30 preferably includes a locking feature 55 that facilitates holding staple 5 in its strained state and allows for easy insertion of staple 5 into a prepared fracture site (see below) Note that locking feature 55 is preferably configured so that the surgeon can strain the staple to different degrees, thereby (i) enabling the surgeon to tailor the compressive force (e.g., by bending only legs 15, or by bending legs 15 and straining bridge 10), and (ii) enabling the surgeon to tailor the amount of recoverable strain established across the fracture line (e.g., by varying the amount that bridge 10 is stretched), depending on bone quality.

Figure 5:
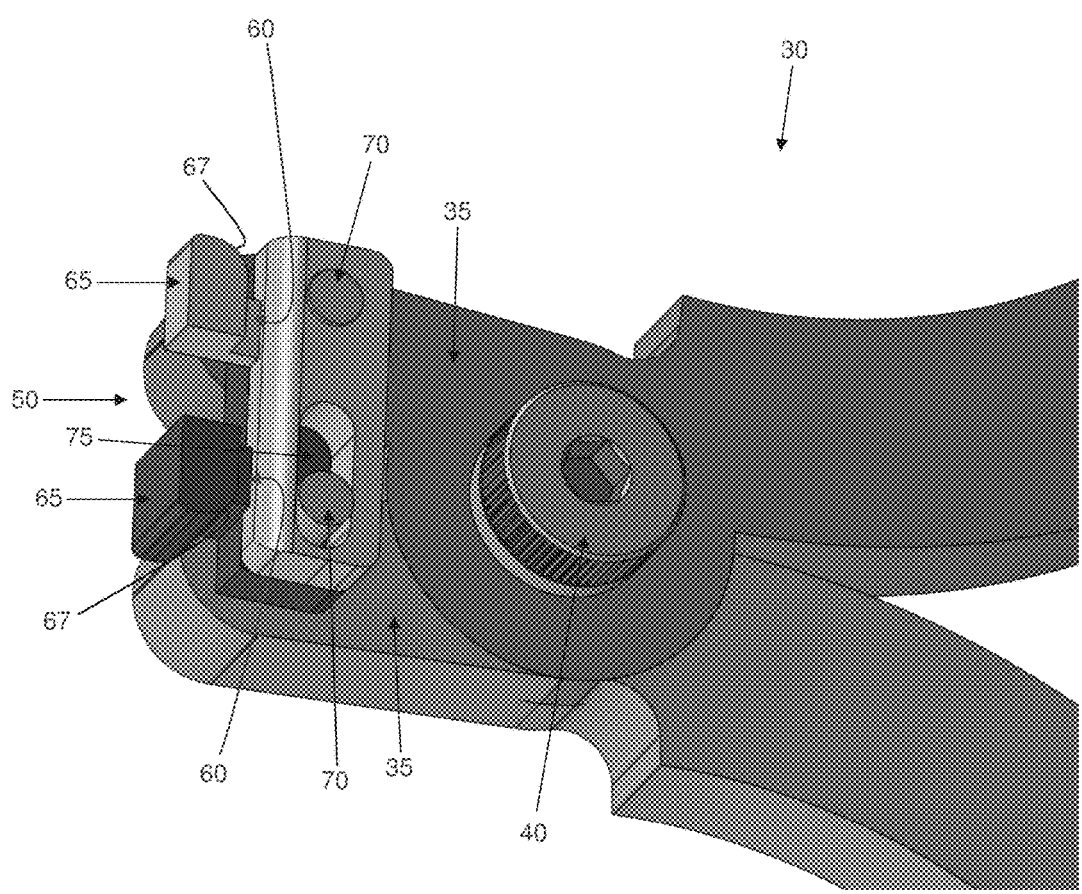

FIG. 5 shows a close-up of staple mount 50 of delivery device 30. Staple mount 50 comprises a channel 60 that receives bridge 10 of staple 5, and two staple-stretching linkages 65 which sit distal to, and help define, channel 60. The radii 67 of staple-stretching linkages 65 mate with the curved hinge regions 20 of staple 5 when the legs 15 of the staple have been strained (i.e., bent) outward to a position substantially perpendicular to the longitudinal axis of bridge 10. Each staple-stretching linkage 65 is connected to the arms 35 by a pin 70. Pins 70 slide in a channels 75 provided on the staple-stretching linkages 65 (i.e., a first pin 70 mounted to a first staple-stretching linkage 65 slides in a channel 75 of the second staple-stretching linkage 65, and a second pin 70 mounted to the second staple-stretching linkage 65 slides in the channel 75 of the first staple-stretching linkage 65). Channels 75 are sized to limit the maximum amount of strain which may be imposed on bridge 10 of staple 5 by delivery device 30 (i.e., channels 75 limit the extent to which bridge 10 of staple 5 may be stretched).

Figure 6:
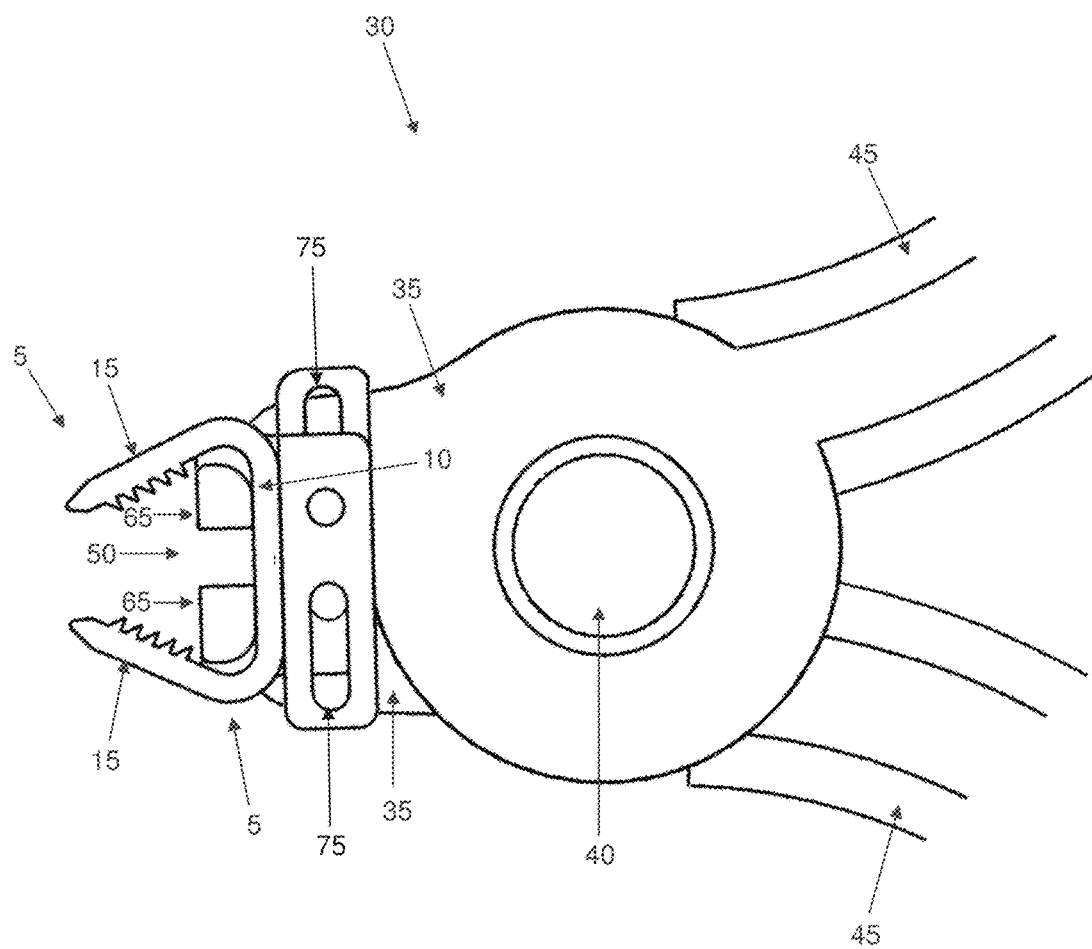
FIGS. 6 and 7 are schematic views showing the delivery device of FIGS. 4 and 5 being used with the novel staple shown in FIG. 1 to elastically strain (i.e., stretch) the bridge of the staple and elastically bend the legs of the staple.
Figure 7:
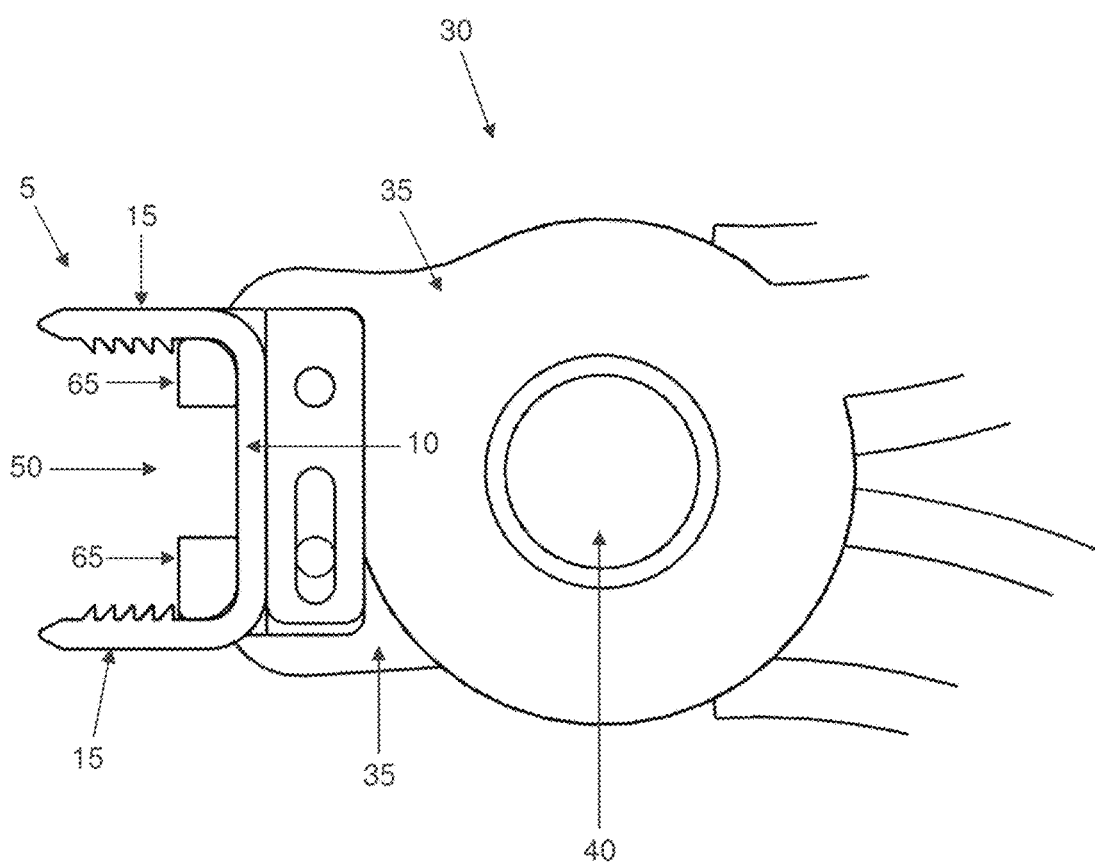

FIGS. 6 and 7 show staple 5 being loaded onto delivery device 30 and staple 5 being strained, i.e., bridge 10 being stretched and legs 15 being bent so that they are perpendicular to the longitudinal axis of bridge 10. More particularly, FIG. 6 shows staple 5 loaded onto staple mount 50 of delivery device 30 while staple mount 50 of delivery device 30 is in its closed (i.e., non-staple-straining) position. This is done by positioning bridge 10 of staple 5 in channel 60 of staple mount 50. Note that in this position, legs 15 of staple 5 are in their unbiased, pointed inward position. FIG. 7 shows staple 5 after handles 45 of delivery device 30 have been moved together, so that staple mount 50 is in its open (i.e., staple-straining) position. This is done by moving handles 45 of delivery device 30 together, thereby forcing staple-stretching linkages 65 of staple mount 50 apart, and causing bridge 10 of staple 5 to be stretched and causing legs 15 of staple 5 to be positioned substantially perpendicular to the longitudinal axis of bridge 10.

Note that with delivery device 30, the delivery device is constructed so that upon squeezing handles 45, the legs of the staple are first bent to perpendicular and then, when the legs of the staple are substantially perpendicular, the bridge of the staple is elongated.

Note that staple 5 is configured so that the force that is generated as staple 5 reconfigures (i.e., as bridge 10 foreshortens and legs 15 bend inward) is less than the "tear through" force of the bone receiving legs 15, i.e., staple 5 is specifically engineered so as to not "tear through" the bone tissue when attempting to reconfigure. Delivery device 30 preferably includes the aforementioned locking feature 55 which enables the surgeon to control the extent to which the staple is strained (e.g., to bend only the legs of the staple, or to both bend the legs of the staple and strain the bridge of the staple, and to control the extent to which the bridge is stretched), thereby allowing the surgeon to tailor the compressive forces and recoverable strain imposed on the anatomy, depending on bone quality. The compressive forces of staple 5 can be controlled by modulating the material properties of the staple and/or the geometry of the staple.

The percentage of cold work in the shape memory material forming staple 5 affects the compressive force generated by the reconfiguring staple. As the percentage of cold work increases, the compression force declines. A staple should, preferably, have between about 15% and 55% cold work to control the recovery force of the staple; however, other degrees of cold work may be used, and/or the material may not be cold worked at all.

Another material property that affects the staple's compression force is the temperature differential between the body that the staple will be implanted into (assumed to be 37° C., which is the temperature of a human body) and the austenite finish temperature of the shape memory material forming staple 5. A smaller temperature differential between the two will result in the staple generating a smaller compressive load; conversely, a larger temperature differential between the two will result in the staple generating a larger compressive load. The shape memory material that the staple is made out of should, preferably, have an austenite finish temperature of greater than about −10° C., resulting in a temperature differential of about 47° C. when the staple is implanted (assuming that the staple is implanted in a human body).

Staple geometry also affects the compression forces generated. The cross-sectional area of bridge 10, and the cross-sectional area of legs 15, affects the compression forces generated by the reconfiguring staple. As the cross-sectional areas increase, so do the compression forces that the reconfiguring staple will generate.

The staple legs are critical for transmitting the compression force to the bone without "tearing through" the bone. The height, width, and length of the staple legs, and the geometry of the staple legs, are all significant relative to the staple's ability to not "tear through" the bone. Staple legs with greater surface area are better able to distribute the compression force and thus not "tear through" the bone.

Figure 8:
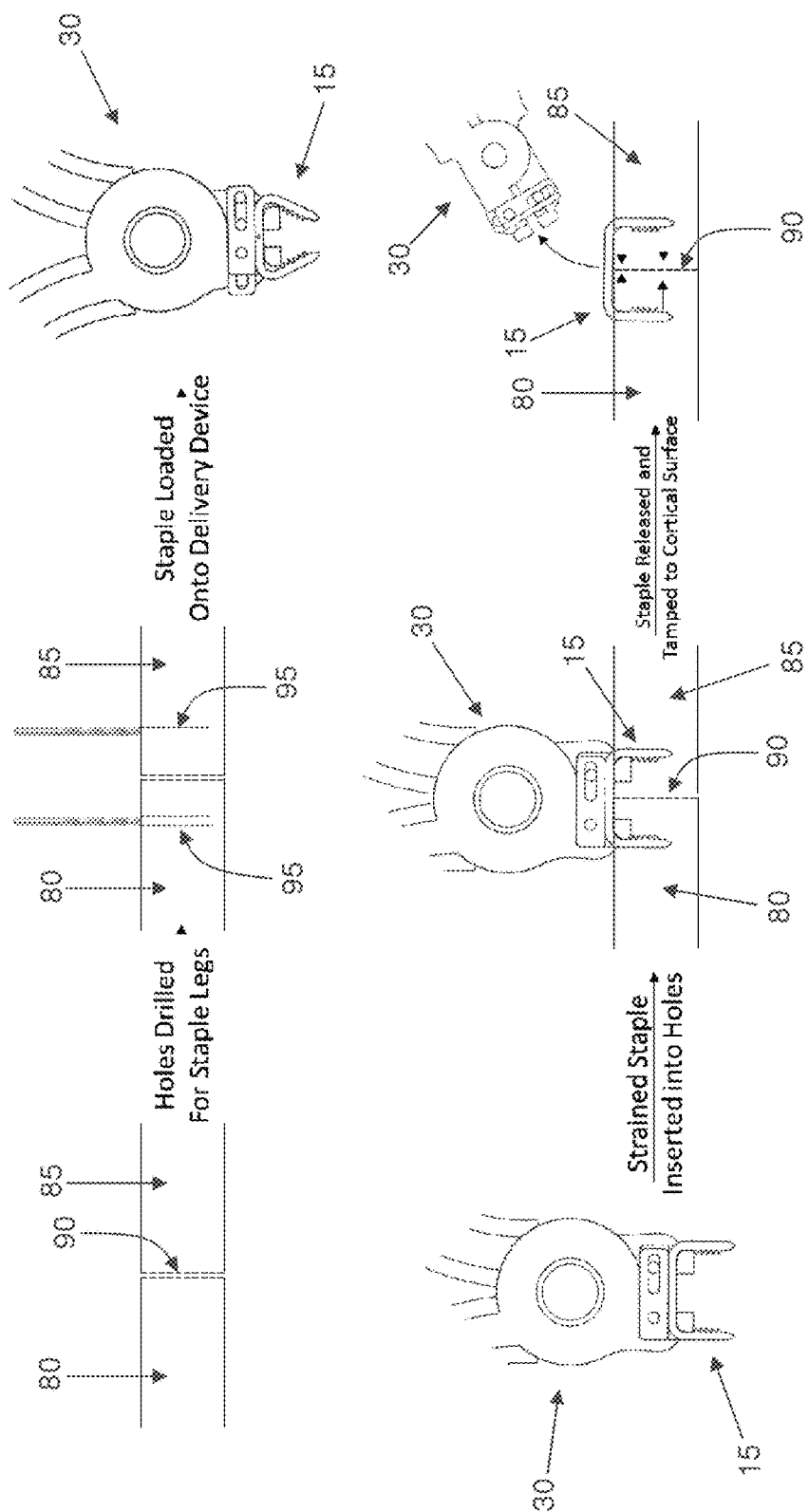
FIG. 8 is a schematic view showing how the novel staple of FIG. 1 may be used to generate and maintain a greater, and more uniform, compression between bone fragments so as to aid in fracture healing.

FIG. 8 shows how staple 5 may be used to reduce a fracture and generate and maintain greater, and more uniform, compression between bone fragments 80 and 85 to aid in fracture healing.

More particularly, the fracture 90 to be fused is first re-approximated and reduced. A drill guide (not shown) of the sort well known in the art is used to drill two holes 95 the correct distance apart to accommodate the legs 15 of the strained staple 5. Staple 5 is loaded onto delivery device 30, and delivery device 30 is used to stretch bridge 10 and straighten legs 15 of staple 5 (i.e., by squeezing together handles 45). While still on delivery device 30, legs 15 of staple 5 are placed into the pre-drilled holes 95. Staple 5 is then released from delivery device 30, which allows the stretched bridge 10 of staple 5 to foreshorten so as to apply compression to the fracture line, and which allows the strained legs 15 of staple 5 to "kick in" and thereby apply additional inward pressure across the fracture line 90. Thus, staple 5 applies more uniform compression across the fracture site, generating compression across both the cortical and intramedullary surfaces, using the compressive forces generated by the foreshortening bridge 10 of the strained staple 5 and using the compressive forces generated by inwardly bending legs 15 of the strained staple 5.

Significantly, when bridge 10 and legs 15 of staple 5 generate a compressive force, both the cortical regions of the bone fragments and the cancellous regions of the bone fragments are pulled together. This provides a superior balance of compression across different regions of the bone.

It should also be appreciated that, if desired, staple 5 can be used to attach soft tissue to bone (e.g., to attach a rotator cuff to bone).

It should be appreciated that delivery device 30 may not always seat the staple with the bridge of the staple seated directly against the cortical surface of the bone (i.e., the bridge of the staple may sit slightly above the cortical surface of the bone). Therefore, a tamp of the sort well known in the art may be used to fully seat the staple bridge against the cortical surface of the bone.

Figure 8B:
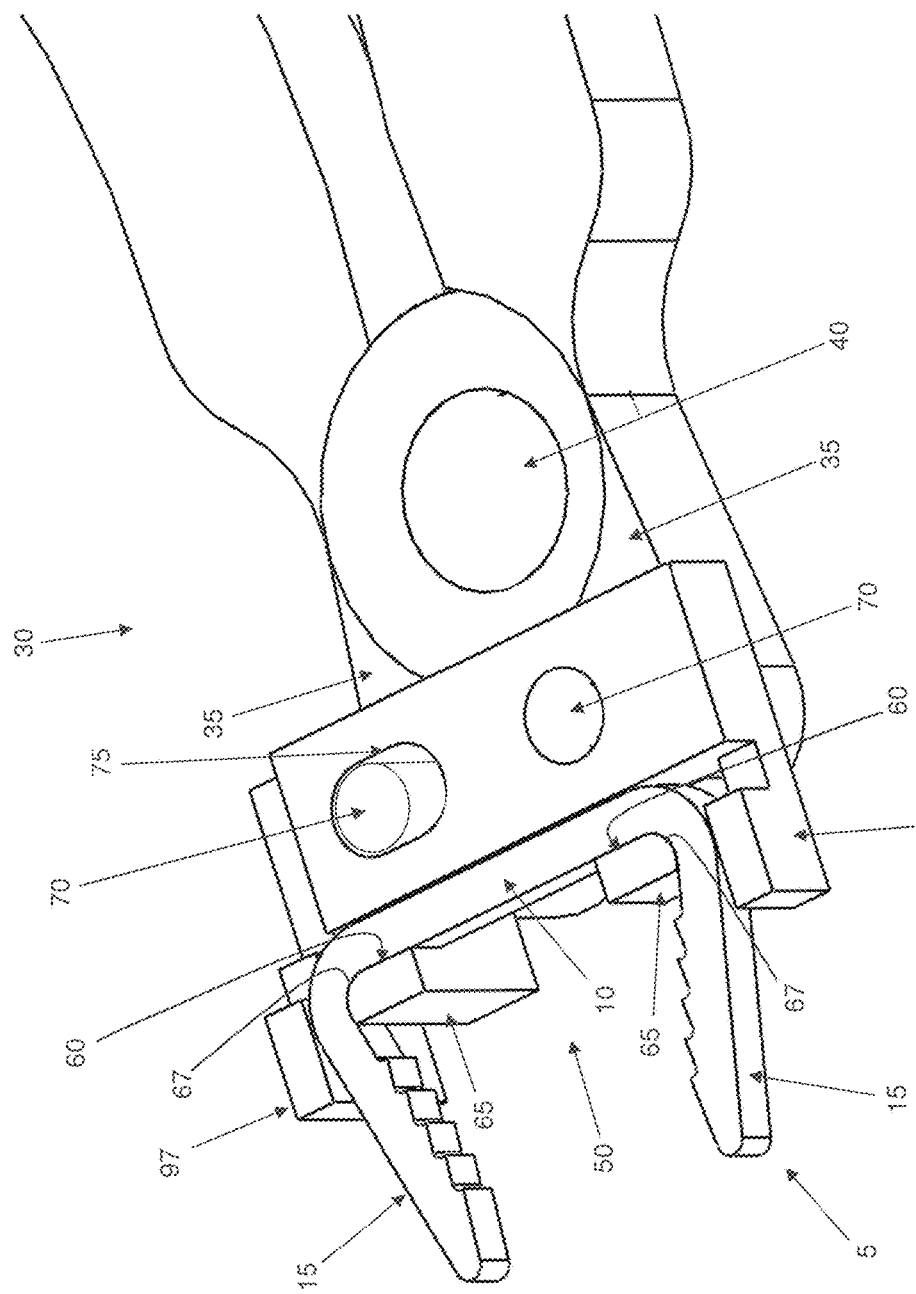
Figure 8C:
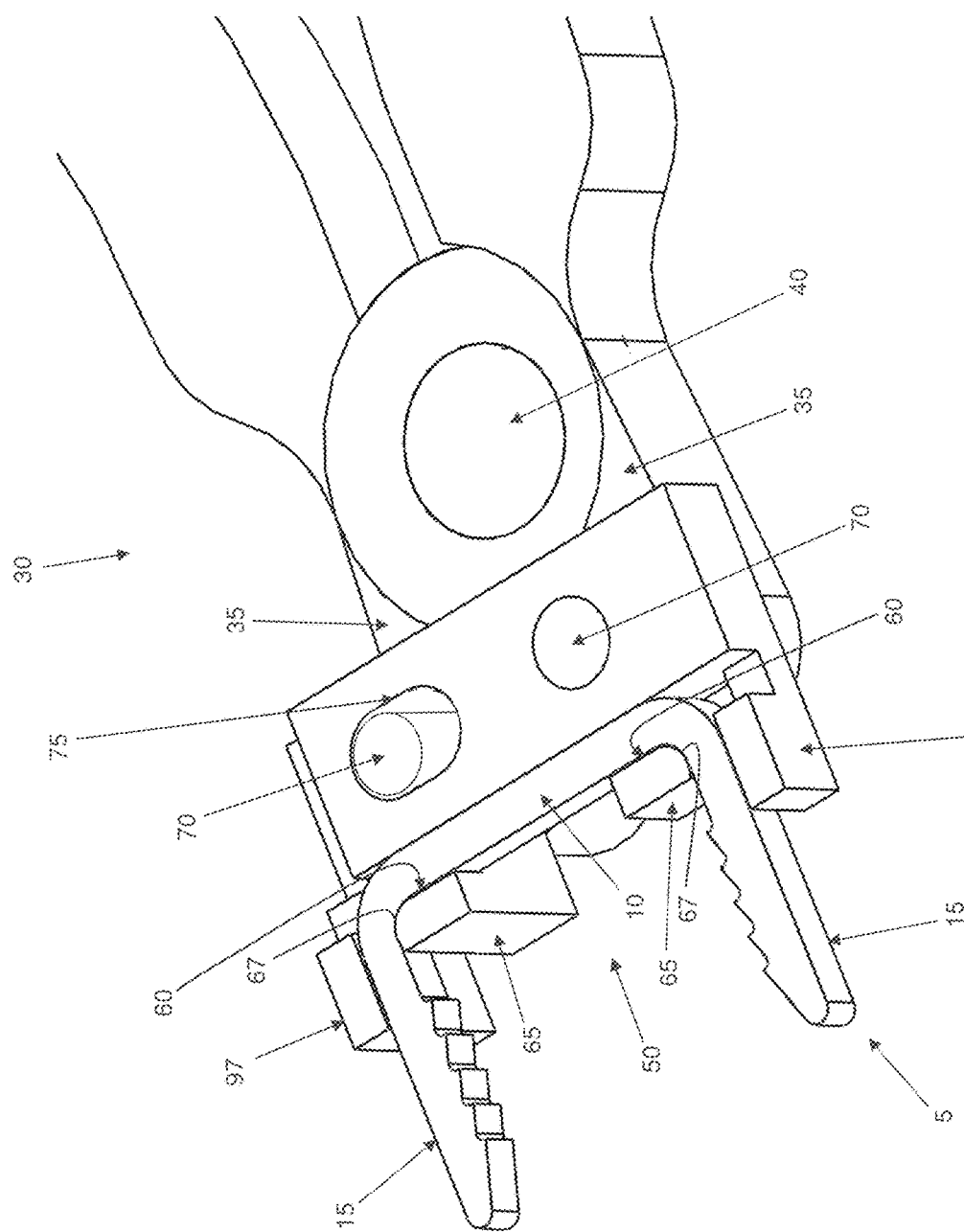

In some circumstances it can be desirable to modify delivery device 30 so as to ensure that legs 15 do not be bent past 90 degrees (relative to the longitudinal axis of bridge 10) when staple 5 is strained. More particularly, in some constructions, staple 5 can require more force to stretch bridge 10 than to bend legs 15. In this circumstance, there is the possibility that legs 15 will be bent to 90 degrees (relative to the longitudinal axis of bridge 10) and then, as bridge 10 is stretched, legs 15 may be bent past 90 degrees (relative to the longitudinal axis of bridge 10). Therefore, it can be desirable to provide means for preventing legs 15 from being bent past 90 degrees (relative to the longitudinal axis of bridge 10). To this end, and looking now at FIGS. 8A, 8B and 8C, delivery device 30 may be constructed so that its staple-straining linkages 65 are each formed with an outboard constraint 97, whereby to prevent legs 15 from being bent past 90 degrees (relative to the longitudinal axis of bridge 10) when the staple is strained.

In one preferred form of the invention, staple 5 and delivery device 30 are provided in the form of a sterilized kit. The kit may include additional instruments to aid in the implantation of the staple (e.g., k-wire, drill bit, staple size guide, tamp, etc.).

In the foregoing discussion, staple 5 is strained so that, upon deployment in the bone, it will provide compression across a fracture line. However, it should also be appreciated that, if desired, staple 5 can be configured to provide a distraction force to a bone. In this situation, staple 5 can be configured and strained so that bridge 10 can be compressed, and/or legs 15 can be bent outward, such that when staple 5 is deployed in bone, the reconfiguring staple can apply a distraction force to the bone, whereby to cause the bone to grow and thereby elongate.

Novel Staple Comprising Malleable Bridge with Two Elastic Legs

As discussed above, staple 5 is manufactured from a shape memory material (e.g., a material capable of exhibiting superelasticity and/or a temperature-induced shape change). The shape memory material may be a metal alloy (e.g., Nitinol) or a polymer (e.g., appropriately processed PEEK). In this respect it should be appreciated that staple 5 can be manufactured out of a single piece of shape memory material (i.e., so as to create an integral, monolithic structure), and the different regions of the staple worked differently, in a metallurgical sense, so that different regions of the staple have different mechanical properties and exhibit different mechanical characteristics, even as they form a single, integral, monolithic structure.

In one form of the invention, and as discussed above, staple 5 can be manufactured so that bridge 10 is elastic, legs 15 are elastic, and curved hinge regions 20 are elastic, in which case bridge 10 can be elastically deformed, and legs 15 can be elastically deformed, so that both bridge 10 and legs 15 provide compression to the fracture site after implantation. In this form of the invention, bridge 10 and legs 15 may be worked, metallurgically, so that they have the same or different mechanical properties.

However, in another form of the invention, staple 5 can be manufactured so that bridge 10 is malleable and non-superelastic (e.g., fully annealed Nitinol, or martensitic Nitinol with an austenite start temperature greater than body temperature), and legs 15 and hinge regions 20 are superelastic (e.g., austenite but capable of forming stress-induced martensite). This allows the malleable bridge 10 of staple 5 to be inelastically bent (i.e., to take a set) to accommodate a particular geometry of the cortical anatomy, while still allowing the superelastic legs 15 of the staple to generate compression. By way of example but not limitation, many bones exhibit an hour-glass surface profile; moreover, certain orthopedic indications (e.g., an Akin Osteotomy) often results in a cortical surface that is concave when the bones are re-approximated. In these situations, a staple with a straight bridge will not sit flush on the bone surface, which can lead to patient discomfort. In this respect it should also be appreciated that where bridge 10 is malleable and legs 15 are superelastic, legs 15 of staple 5 may be manufactured at a more acute angle (FIG. 10) so as to allow for adequate fracture compression and reduction in the event that bridge 10 must be bent downward (e.g., deformed to a concave position) to meet the anatomical structure of the cortical bone.

Figure 9:
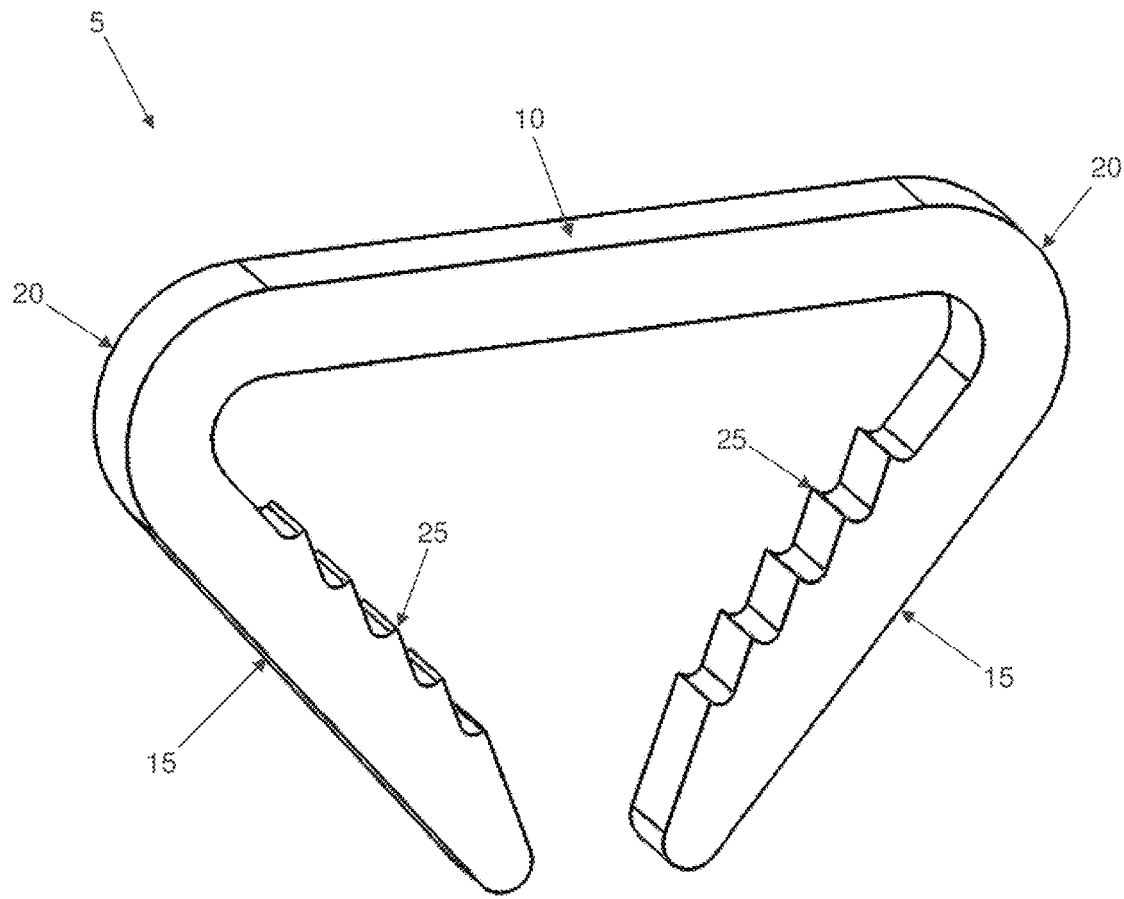
Figure 10:
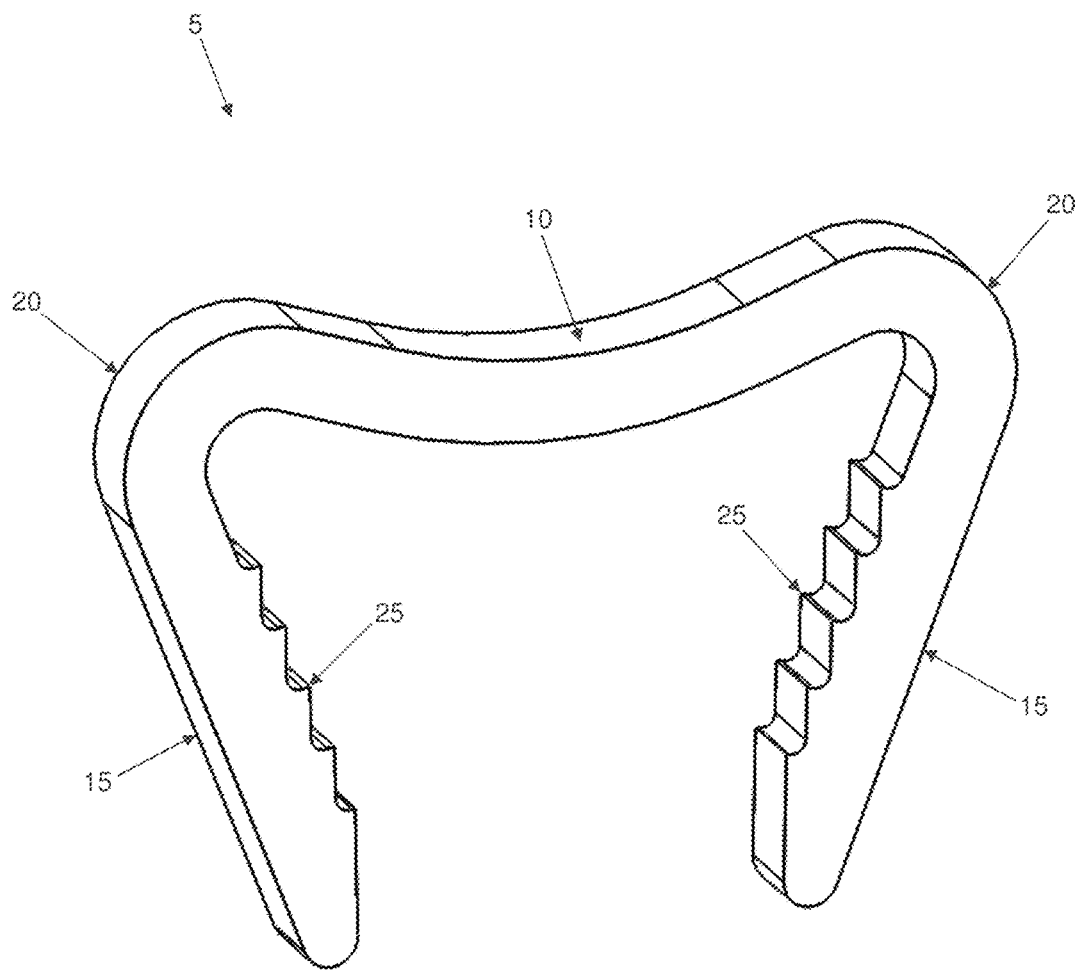

See FIG. 9, which shows a monolithic staple 5 where bridge 10 is malleable and legs 15 are superelastic, and where staple 5 is shown in its unbent and unstrained condition; and FIG. 10, where bridge 10 of staple 5 has been bent to give it an altered configuration. Note that staple 5 shown in FIGS. 9 and 10 is preferably formed out of a single piece of shape memory material, whereby to form a single, integral, monolithic structure, with the single piece of shape memory material having different regions of the staple worked differently, in a metallurgical sense, so that different regions of the staple have different mechanical properties and exhibit different mechanical characteristics, i.e., bridge 10 is malleable and legs 15 are superelastic.

Figure 10A:
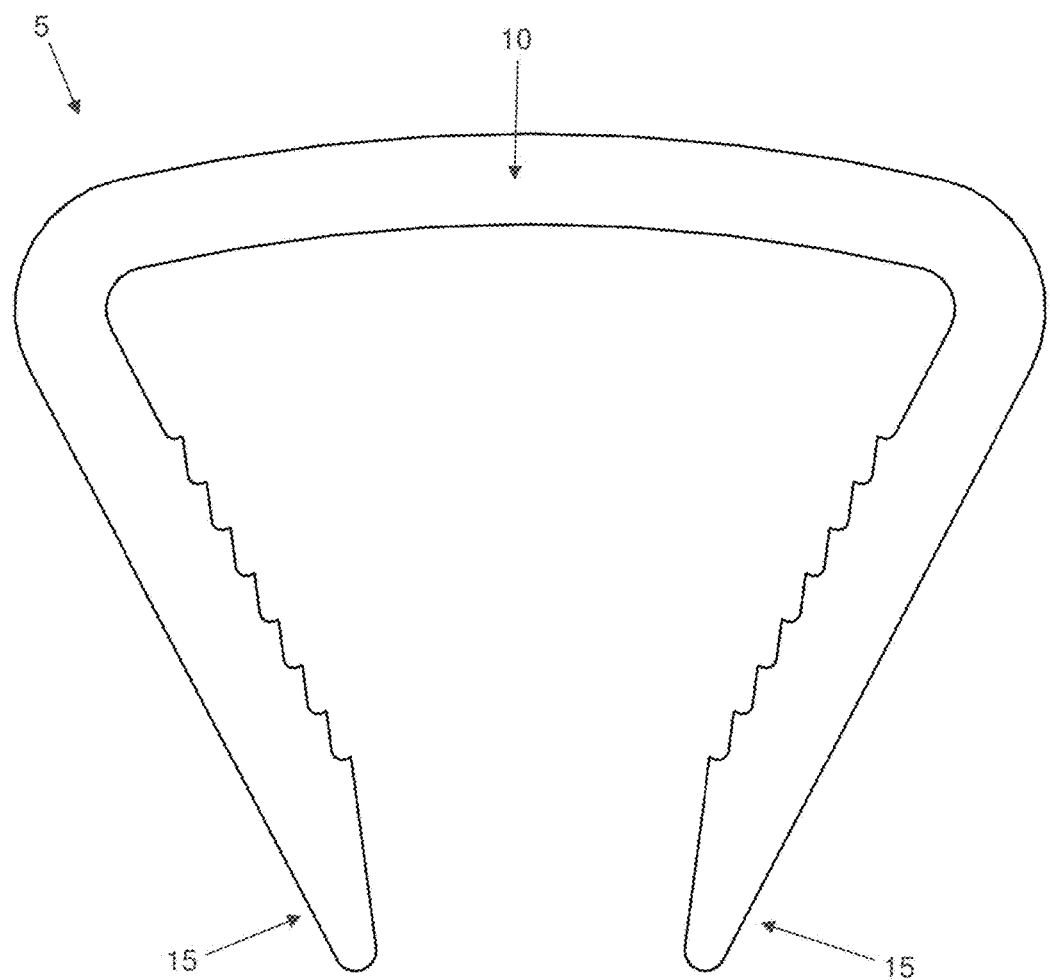
FIG. 10A is a schematic view of another novel staple formed in accordance with the present invention, wherein the staple has a bridge that is convex.

It may be desirable for staple 5 to start with a bridge that is convex, e.g., such as the staple 5 shown in FIG. 10A. This will allow the bridge of the implanted staple to sit flush with the cortical bone surface if the bone surface is largely planar. More particularly, if the bridge of staple 5 were to be linear, and the legs strained and the staple inserted into a prepared fracture site where the cortical surface is largely planar, the resulting implanted staple could have two small "humps" at the outer ends of the bridge, i.e., at the bridge-hinge interface. Starting with a convex-shaped bridge (i.e., such as is shown in FIG. 10A) largely eliminates these "humps".

Thus, in a second form of the invention, staple 5 is formed out of a single piece of shape memory material (i.e., so as to form a single, integral, monolithic structure), with the shape memory material being worked so that bridge 10 is malleable (e.g., fully annealed Nitinol, or martensitic Nitinol with an austenite start temperature greater than body temperature) and legs 15 are superelastic (e.g., austenite but capable of forming stress-induced martensite), such that bridge 10 of staple 5 may be bent to contour to the surface of the bone while the compressive force generated by the superelastic legs 15 of the staple are used to help fuse the bone.

Figure 11:
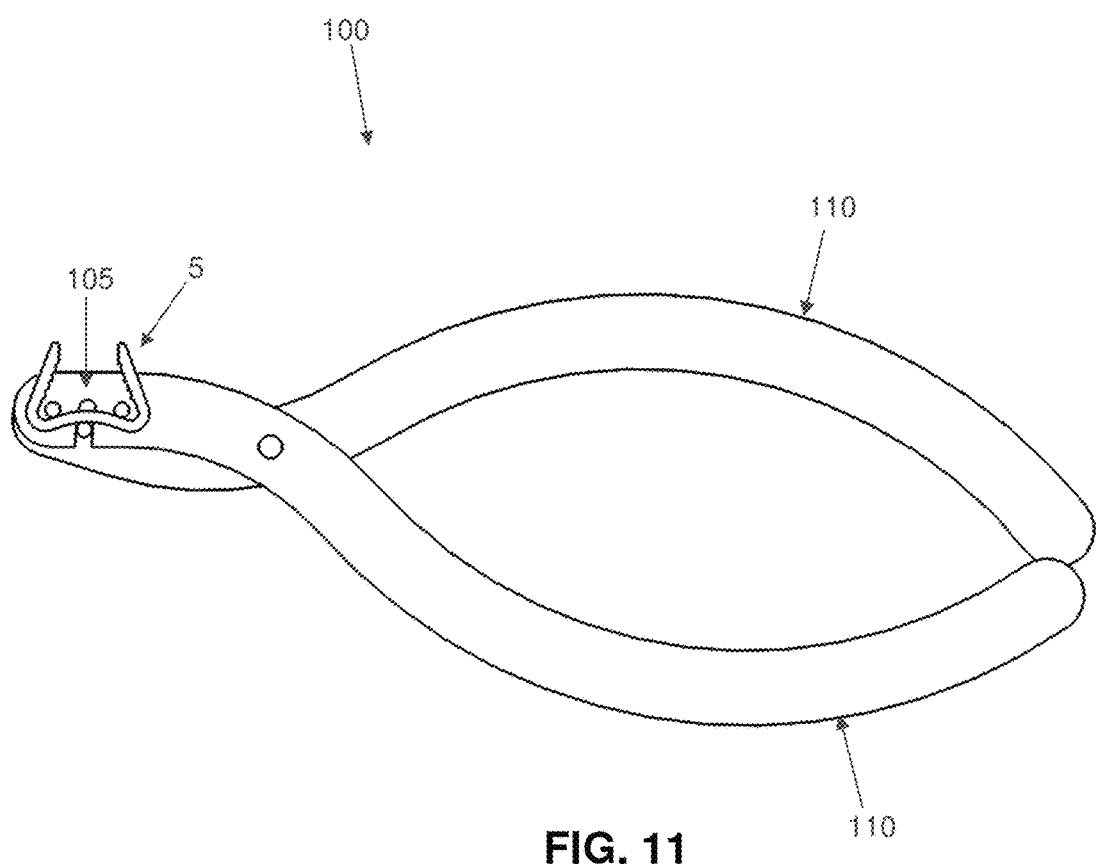
FIGS. 11 and 12 are schematic views showing an exemplary bending device which may be used with the novel staple shown in FIGS. 9 and 10 to inelastically bend the bridge of the staple to more appropriately conform to the surface profile of the cortical bone.

A bending device can be used to bend bridge 10 of staple 5 prior to implantation of the staple. An exemplary bending device 100 is shown in FIG. 11. Bending device 100 is essentially a modified plier assembly. Staple 5 is placed into the bending fixture 105 of bending device 100; compressing the handles 110 causes bridge 10 of staple 5 to be bent to better meet the shape of the cortical bone surface.

Figure 12:
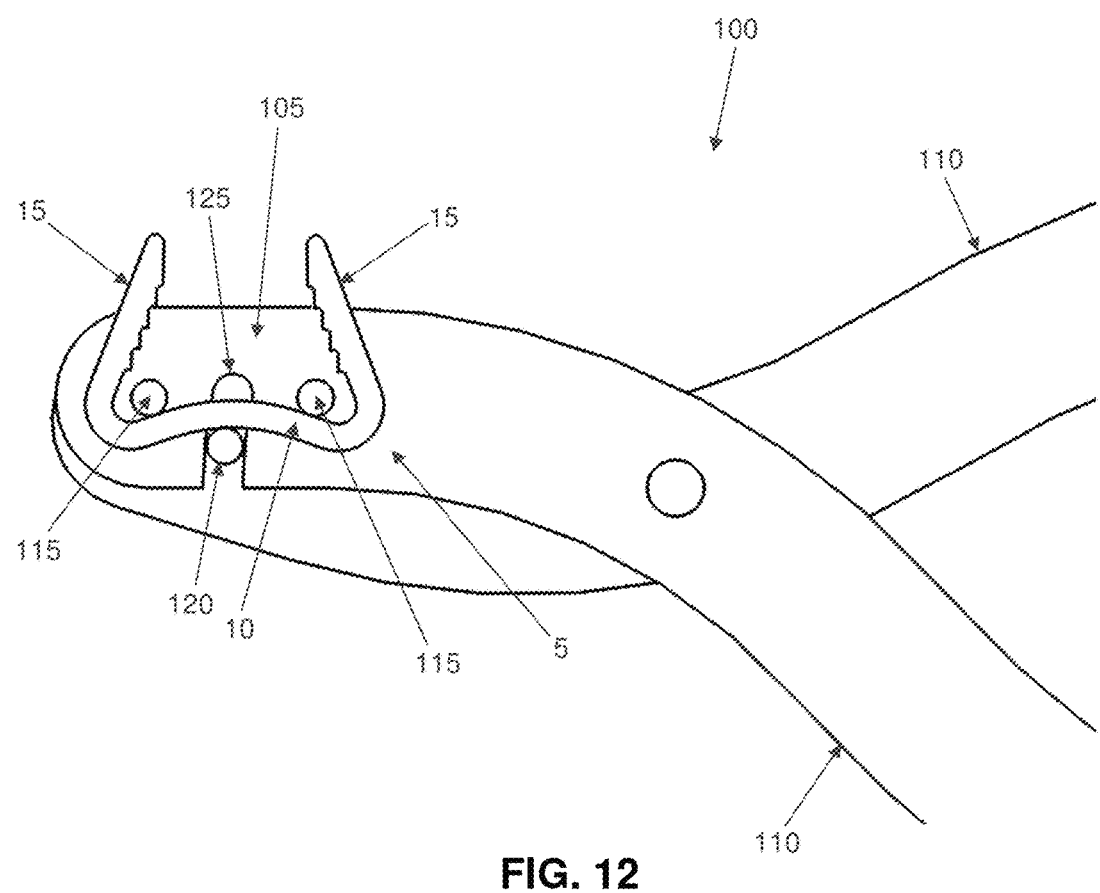

More particularly, FIG. 12 shows a close-up of bending fixture 105 of bending device 100. Two pins 115 are used to locate the staple, and a third pin 120 is used to bend the bridge of the staple when the handles 110 of bending device 100 are compressed. A channel 125 in bending fixture 105 both directs the shape of the contour while also serving to limit the maximum bend imposed on the bridge of the staple.

Figure 13:
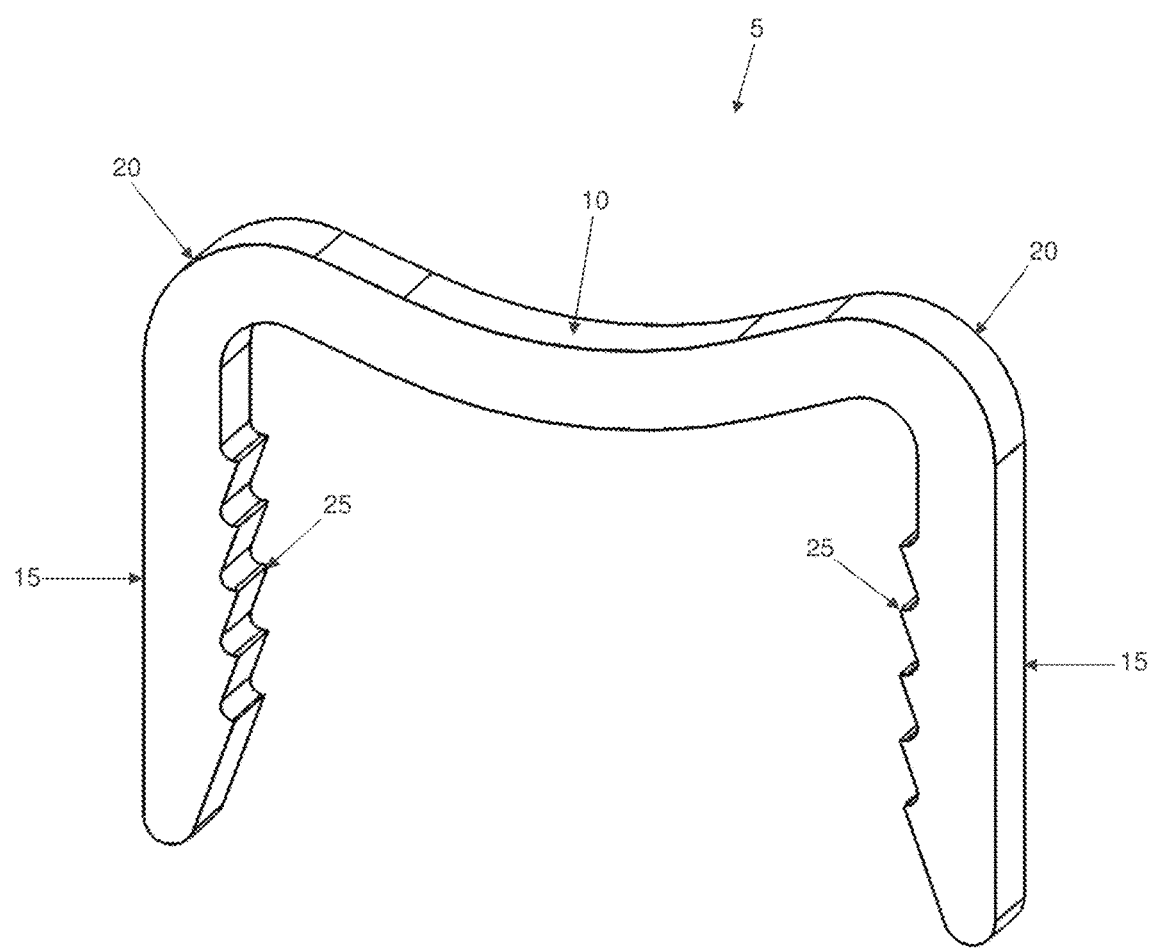
FIG. 13 is a schematic view which shows the staple of FIGS. 9 and 10 after the bridge of the staple has been inelastically bent and after the legs of the staple have been elastically strained into a parallel condition.
Figure 14:
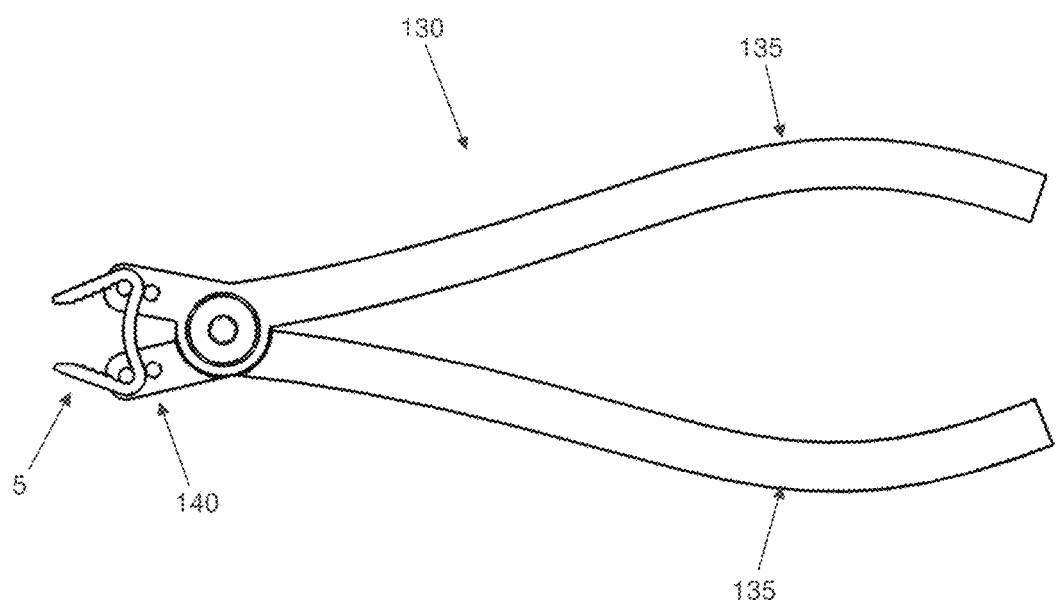
FIGS. 14-16 are schematic views showing a plier assembly which may be used with the novel staple shown in FIGS. 9 and 10 to elastically strain (i.e., stretch) the legs of the staple after the bridge of the staple has already been inelastically bent.

After the bridge of the staple has been bent to the desired geometry (e.g., the geometry shown in FIG. 10), the legs of the staple can be strained open (e.g., to the geometry shown in FIG. 13) so as to allow the bent, strained staple to be inserted into the prepared fracture site. By way of example but not limitation, and looking now at FIG. 14, the bent staple may be strained using a plier assembly 130 comprising a pair of handles 135 and a straining fixture 140. The previously-bent staple is placed into straining fixture 140, and compressing handles 135 causes the staple's legs 15 to be strained opened to parallel.

Plier assembly 130 is also used to insert the staple into the bone after the legs of the staple have been strained open to substantially parallel.

Figure 15:
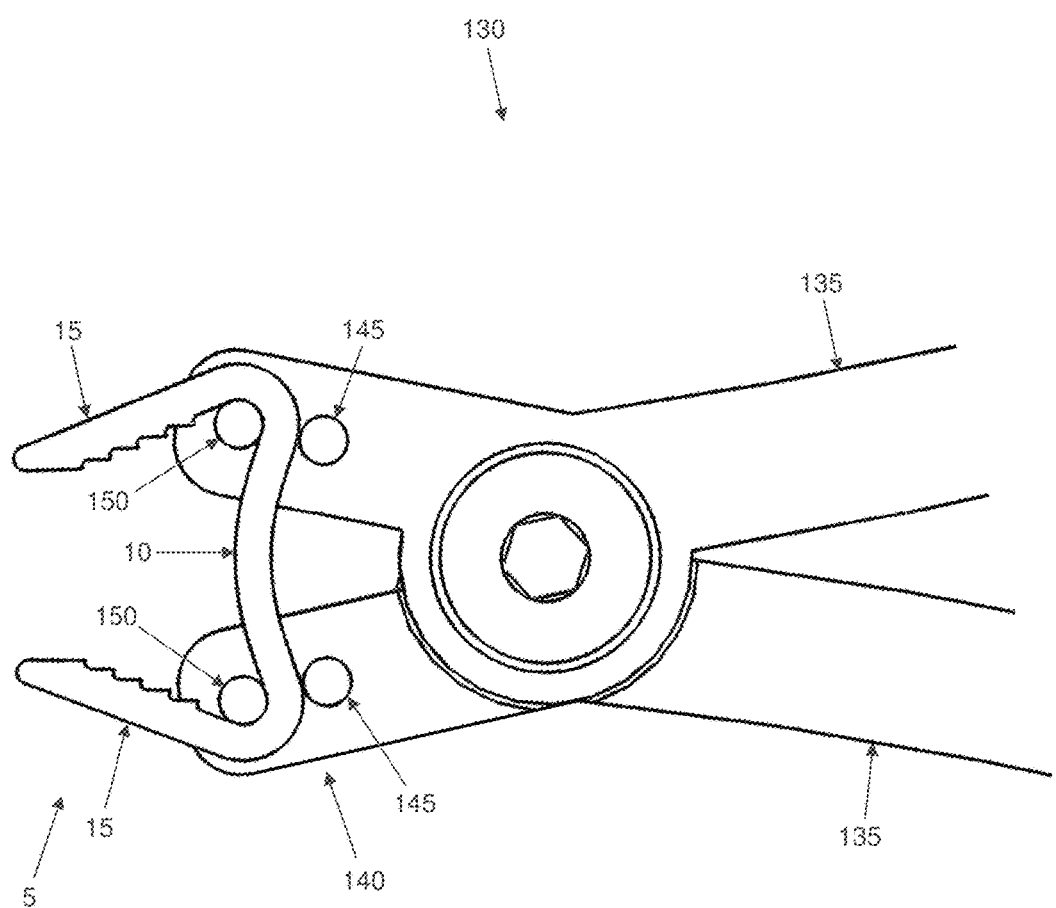
Figure 16:
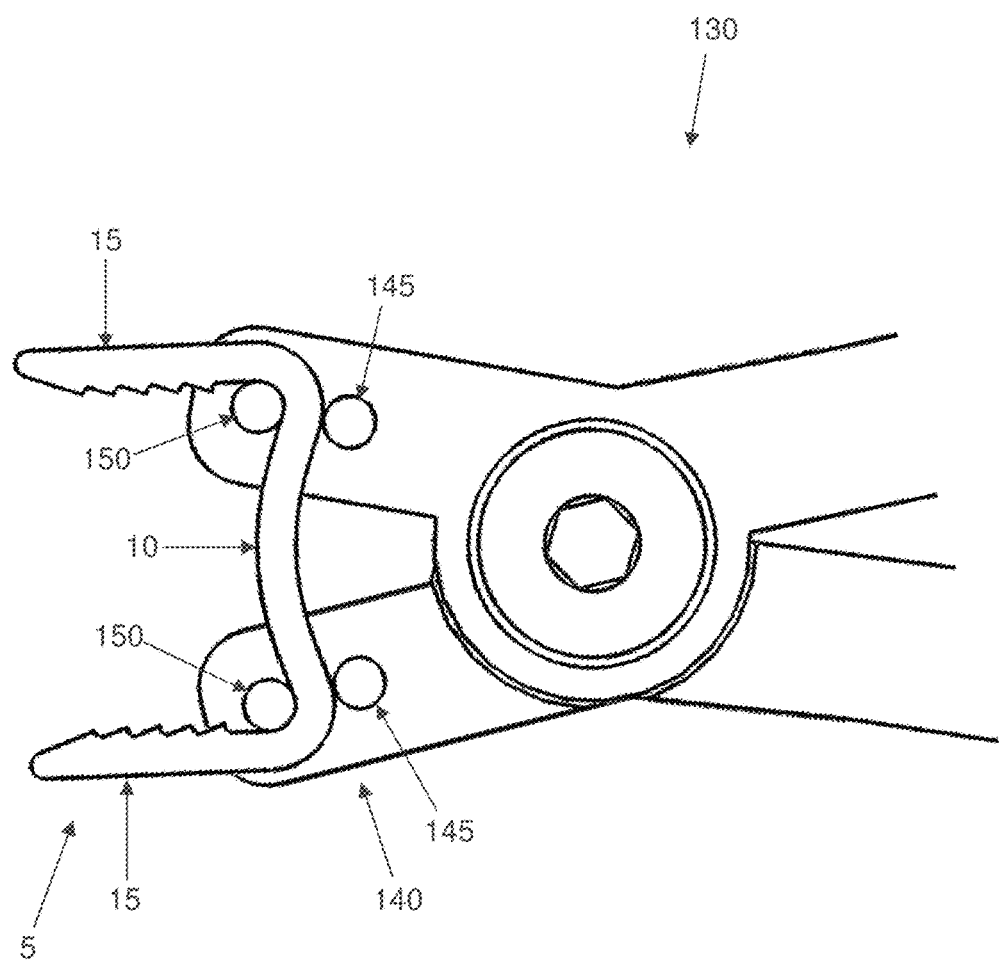

FIGS. 15 and 16 show the construction and function of straining fixture 140 in greater detail. Staple 5 is supported by two internal pins 145 and two external pins 150. Compressing handles 135 cause the staple legs to move from an inward-pointing configuration (FIG. 15) to a more open (e.g., parallel) state (FIG. 16). The previously-bent staple, with the legs now strained to the open state, is then ready for implantation across the fracture line. When implanted in bone and thereafter released from plier assembly 130, the strained legs 15 of staple 5 then kick inward, reducing the fracture and generating and maintaining compression across the fracture.

Figure 17:
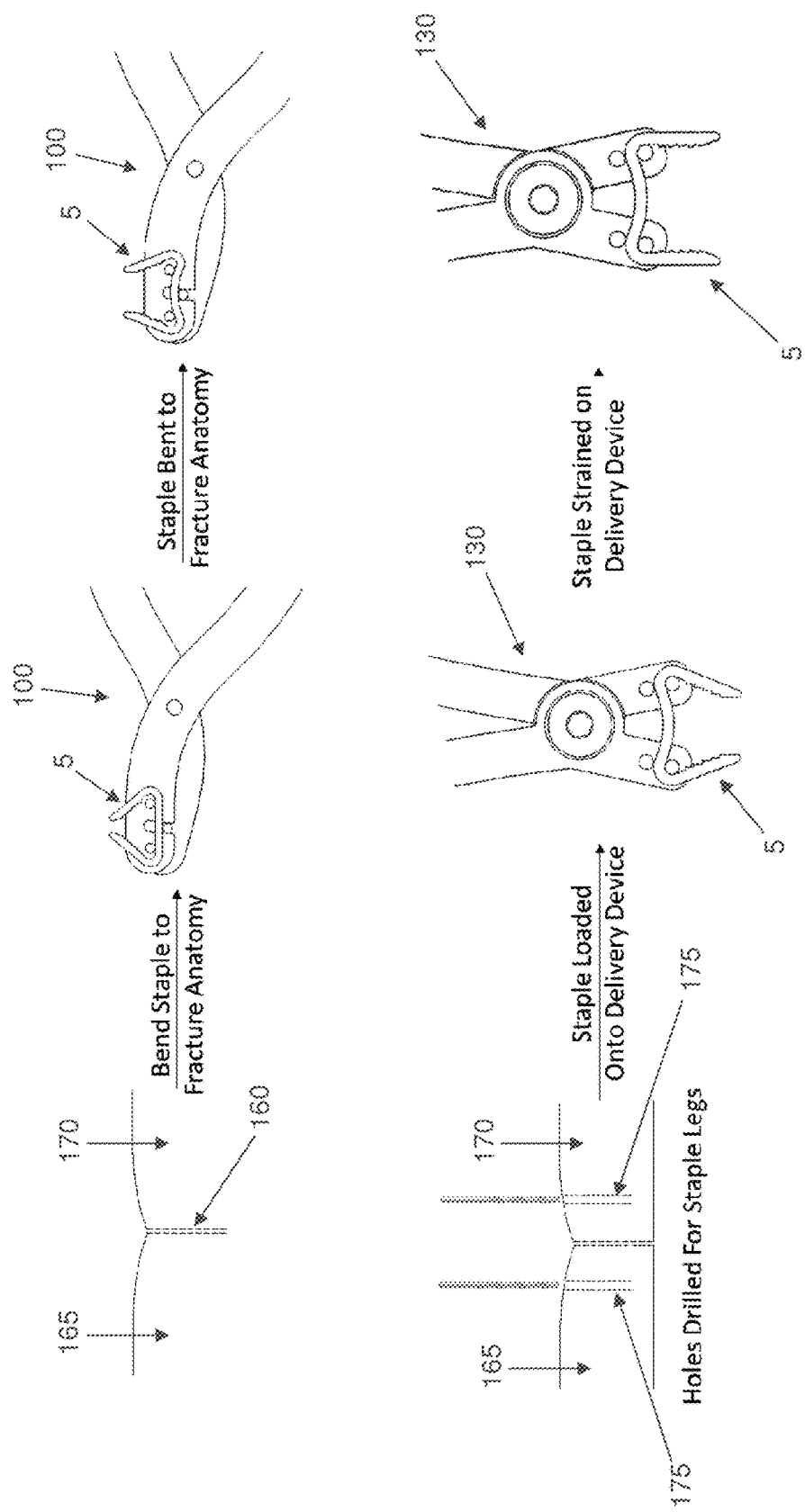
FIGS. 17 and 18 are schematic views showing how the novel staple shown in FIGS. 9 and 10 may have the bridge of the staple inelastically bent to conform to the surface profile of a bone, the legs of the staple elastically bent into a parallel condition, and the staple thereafter deployed in bone so as to provide compression across a fracture.
Figure 18:
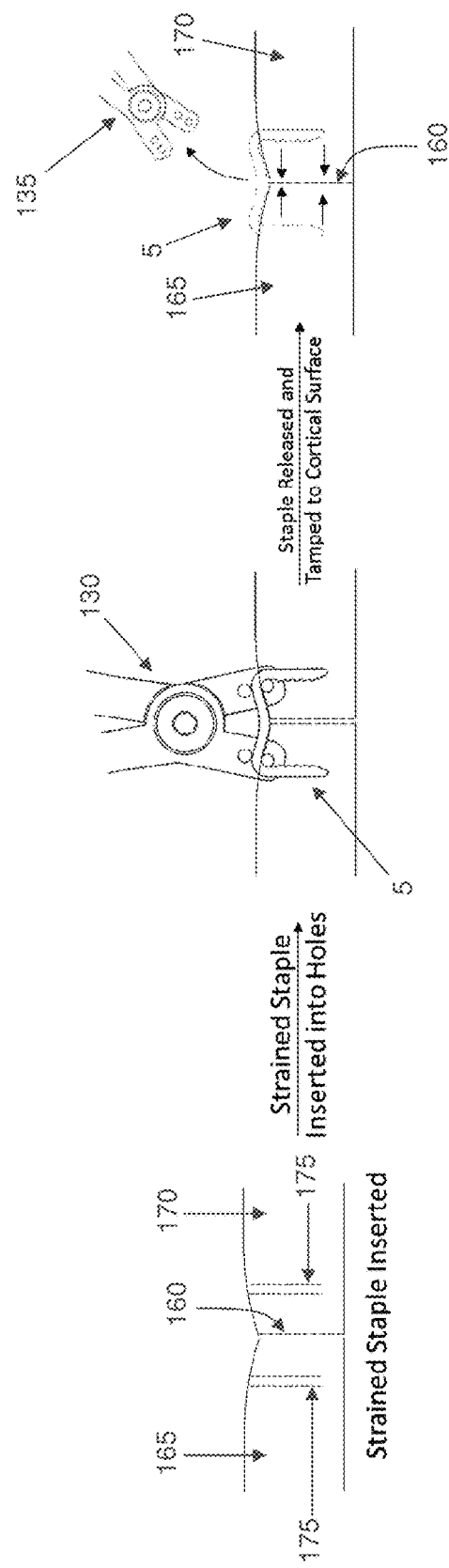

FIGS. 17 and 18 show how a staple formed out of a shape memory material, with its bridge being malleable (e.g., fully annealed Nitinol, or martensitic Nitinol with an austenite start temperature greater than body temperature) and its legs being superelastic (e.g., austenite but capable of forming stress-induced martensite), may be used to reduce a fracture 160 between two bone fragments 165, 170 and generate and maintain compression across the fracture. Significantly, because the bridge of the staple is malleable and the legs of the staple are superelastic, the bridge of the staple can be first bent to match the surface profile of the bone while enabling the superelastic legs of the staple to be elastically strained to provide the compressive force across the fracture.

Looking now at FIGS. 17 and 18, staple 5 is first loaded onto bending device 100 and the bridge of the staple is bent to accommodate the surface profile of the patient's cortical bone anatomy. The surgeon may use fluoroscopy or trial-and-error to bend the bridge of the staple to the appropriate configuration. With the bridge of the staple appropriately bent, a drill guide (not shown) is used to drill holes 175 into the bone fragments 165, 170 at the appropriate locations on either side of the fracture line 160 to accommodate the strained staple legs. Staple 5 is then loaded onto plier assembly 130, and superelastic legs 15 are then elastically bent to the open state.

With the bridge of the staple inelastically bent into the appropriate configuration and with the legs of the staple elastically strained to substantially parallel, the staple can be inserted into the pre-drilled holes 175 in bone fragments 165, 170. The staple is then released from plier assembly 130 and tamped to sit flush with the cortical surface, with the inelastically bent bridge 10 of the staple more closely matching the surface contour of the bone. The elastically-strained superelastic legs 15 of the staple applies a compressive force across the fracture.

If desired, where the staple is provided with a malleable bridge, the malleable bridge may be bent, or further bent, after the staple has been deployed in bone, e.g., to match, or to more closely match, the surface profile of the bone.

In some circumstances the bone may have a convex profile. In this circumstance, it may be desirable to set the staple so that its bridge has a convex configuration. To this end, and looking now at FIG. 19, there is shown a staple 5 which has been inelastically bent to have a convex bridge 10 and two legs 15.

FIGS. 20 and 21 show another bending device 180 which may be used to bend the bridge of a staple, e.g., the bridge 10 of the staple 5 shown in FIG. 10A. Bending device 180 generally comprises a housing 185 supporting a pair of pins 190. Pins 190 receive staple 5 in the manner shown in FIG. 21. Bending device 180 also comprises a screw mechanism 195 which selectively advances an element 200 toward pins 190 or retracts element 200 away from pins 190. As a result of this construction, when staple 5 is mounted on pins 190, screw mechanism 195 can be used to drive element 200 against bridge 10 of staple 5, whereby to bend the bridge of the staple.

It should also be appreciated that, if desired, staple 5 can be used to attach soft tissue to bone (e.g., to attach a rotator cuff to bone).

It should be appreciated that delivery device 130 discussed above may not always seat the staple with the bridge of the staple seated directly against the cortical surface of the bone (i.e., the bridge of the staple may sit slightly above the cortical surface of the bone). Therefore, a tamp of the sort well known in the art may be used to fully seat the staple bridge against the cortical surface of the bone.

In one preferred form of the invention, staple 5, bending device 100 and/or bending device 180, and delivery device (i.e., plier assembly) 130 are provided in the form of a sterilized kit. The kit may include additional instruments to aid in the implantation of the staple (e.g., k-wire, drill bit, staple size guide, tamp, etc.).

Test Data

Conventional shape memory staples typically generate between about 20N and about 120N of compressive force from the staple legs kicking inward.

The novel staple of the present invention having a stretched bridge as described herein generates a compressive load of greater than the 20N to 120N generated by other like-sized conventional staples, thereby providing significantly increased compressive forces without tearing through or otherwise damaging the bone. Additionally, the compressive force provided by the stretched bridge staple of the present invention is more uniformly distributed across the fracture line (i.e., across the cortical bone and the cancellous bone).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. A staple comprising:
    a malleable bridge configured to be inelastically deformed;
    a first leg connected to said bridge and configured to be elastically bendable; and
    a second leg connected to said bridge and configured to be elastically bendable;
    said first and second legs being connected to said bridge so that they are angled toward one another when they are in an unstrained state,
    wherein said bridge and said first and second legs are integrally formed out of a single piece of shape memory material so as to form a monolithic staple,
    wherein said shape memory material is processed so that said bridge is fully annealed Nitinol or martensitic Nitinol with an austenite start temperature greater than body temperature, and said first and second legs are austenite but capable of forming stress-induced martensite, such that when said bridge is inelastically deformed, and said first and second legs are elastically strained so that they extend substantially parallel to one another, and said first and second legs are disposed in appropriate holes on opposing sides of a fracture line, and when the strain on said staple is thereafter released, compression will be provided across the fracture line by said first and second legs.

2. The staple according to claim 1 wherein said bridge may be inelastically deformed to substantially match a surface profile of one or more structures of bone that have been re-approximated.

3. The staple according to claim 1 wherein said shape memory material comprises Nitinol.

4. The staple according to claim 1 wherein said first leg is connected to said bridge by a first hinge and said second leg is connected to said bridge by a second hinge, and further wherein said first and second hinges are elastically deformable.

5. The staple according to claim 1 wherein said staple comprises more than two legs.

6. The staple according to claim 1 wherein said bridge has a convex configuration prior to implantation.

7. The staple according to claim 1 wherein a bending device is used to bend said bridge of said staple and a delivery device is used to bend said legs of said staple, and insert said staple across the fracture line, and further wherein said staple, said bending device and said delivery device are packaged as a sterilized kit.

8. The staple according to claim 1 wherein a single device is used to bend said bridge of said staple and to bend said legs of said staple and insert said staple across the fracture line, and further wherein said staple and said single device are packaged as a sterilized kit.

9. A method for providing compression across a fracture line, the method comprising:
providing a staple comprising:
a malleable bridge configured to be inelastically deformed;
a first leg connected to said bridge and configured to be elastically bendable; and
a second leg connected to said bridge and configured to be elastically bendable;
said first and second legs being connected to said bridge so that they are angled toward one another when they are in an unstrained state;
inelastically deforming said bridge, and elastically straining said first and second legs parallel to one another;
inserting said first and second legs in appropriate holes on opposing sides of a fracture line; and
releasing the strain on said staple so that compression is provided across the fracture line by said first and second legs.

10. The method according to claim 9 wherein said bridge is inelastically deformed so as to substantially match a surface profile of a bone.

11. The method according to claim 9 wherein said bridge and said first and second legs are integrally formed out of a single piece of shape memory material so as to form a monolithic staple.

12. The method according to claim 11 wherein said shape memory material comprises Nitinol.

13. The method according to claim 11 wherein said shape memory material is processed so that said bridge is fully annealed Nitinol or martensitic Nitinol with an austenite start temperature greater than body temperature, and said first and second legs are austenite but capable of forming stress-induced martensite.

14. The method according to claim 11 wherein said first leg is connected to said bridge by a first hinge and said second leg is connected to said bridge by a second hinge, and further wherein said first and second hinges are elastically deformable.

15. The method according to claim 9 wherein said staple comprises more than two legs.

16. The method according to claim 9 wherein a bending device is used to bend said bridge of said staple and a delivery device is used to bend said legs of said staple, and insert staple across a fracture line, and further wherein said staple, said bending device and said delivery device are packaged as a sterilized kit.

17. The method according to claim 9 wherein a single device is used to bend said bridge of said staple and to bend said legs of said staple and insert said staple across the fracture line, and further wherein said staple and said single device are packaged as a sterilized kit.

* * * * *